(12) United States Patent
Blackaby et al.

(10) Patent No.: US 6,969,716 B2
(45) Date of Patent: Nov. 29, 2005

(54) 5-PHENYL[1,2,4]TRIAZINES AS LIGANDS FOR GABA-A α2/α3 RECEPTORS FOR TREATING ANXIETY OR DEPRESSION

(75) Inventors: Wesley Peter Blackaby, Buckhurst Hill (GB); Simon Charles Goodacre, Benington (GB); David James Hallett, Watford (GB); Andrew Jennings, Sawbridgeworth (GB); Richard Thomas Lewis, Bishops Stortford (GB); Leslie Joseph Street, Little Hallingbury (GB); Kevin Wilson, Bishops Stortford (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 10/769,070

(22) Filed: Jan. 30, 2004

(65) Prior Publication Data
US 2004/0192692 A1 Sep. 30, 2004

(30) Foreign Application Priority Data
Feb. 7, 2003 (GB) .............................. 0302887
May 2, 2003 (GB) .............................. 0310228

(51) Int. Cl.⁷ .................. C07D 253/065; A61K 31/53; A61P 25/22
(52) U.S. Cl. ......................... 514/242; 544/182
(58) Field of Search .......................... 544/182; 514/242

(56) References Cited

FOREIGN PATENT DOCUMENTS

JP         05051369 A2 *   3/1993
WO      WO 00/66568 A1 * 11/2000

OTHER PUBLICATIONS

Konno et al., J. Agric. Food Chem. 43, 838–842, 1995.*
Talanta 24(11), 685–687. CA 89: 35597, 1978.*
Joshi et al., Heterocycles 16(9), 1545–1553.*
O'Rourke et al., Journal of Medicinal Chemistry 20(5), 723–726, 1977.*

* cited by examiner

*Primary Examiner*—Venkataraman Balasubramanian
(74) *Attorney, Agent, or Firm*—J. Eric Thies; Melvin Winokur

(57) ABSTRACT

The present invention provides a compound of formula I, or an N-oxide thereof or a pharmaceutically acceptable salt thereof:

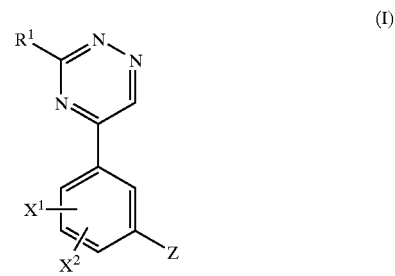

(I)

wherein $X^1$ represents hydrogen, halogen, $C_{1-6}$ alkyl, trifluoromethyl or $C_{1-6}$ alkoxy;

$X^2$ represents hydrogen or halogen;

Z represents hydrogen, halogen, cyano, cyanomethyl, trifluoromethyl, nitro, hydroxy, hydroxy($C_{1-6}$)alkyl, $C_{1-6}$ alkoxy, $C_{1-6}$ alkoxy($C_{1-6}$)alkyl, trifluoromethoxy, trifluoromethylthio, trifluoromethanesulfinyl, formyl, $C_{2-6}$ alkoxycarbonyl, oxopyrrolidinyl, or an optionally substituted aryl, heteroaryl or heteroaryl($C_{1-6}$)alkoxy group; and $R^1$ represents aryl or heteroaryl, either of which groups may be optionally substituted;
pharmaceutical compositions comprising it, its use in therapy and methods of treatment of anxiety and/or depression using it.

10 Claims, No Drawings

5-PHENYL[1,2,4]TRIAZINES AS LIGANDS FOR GABA-A α2/α3 RECEPTORS FOR TREATING ANXIETY OR DEPRESSION

CROSS REFERENCE TO RELATED APPLICATIONS

This application claims priority under 35 U.S.C. § 119 from GB Application No. 0302887.5, filed Feb. 7, 2003 and GB Application No. 0310228.2, filed May 2, 2003.

The present invention relates to a class of substituted triazine derivatives and to their use in therapy. More particularly, this invention is concerned with 5-phenyl[1,2,4]triazine analogues. These compounds are ligands for $GABA_A$ receptors and are therefore useful in the therapy of deleterious neurological complaints.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six α subunits, four β subunits, three γ subunits, one δ subunit, one ε subunit and two ρ subunits.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, δ, ε and ρ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, α1β2γ2, α2βγ1, α2β2/3γ2, α3βγ2/3, α4βδ, α5β3γ2/3, α6βγ2 and α6βδ. Subtype assemblies containing an α1 subunit are present in most areas of the brain and are thought to account for over 40% of $GABA_A$ receptors in the rat. Subtype assemblies containing α2 and α3 subunits respectively are thought to account for about 25% and 17% of $GABA_A$ receptors in the rat. Subtype assemblies containing an α5 subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with a β subunit and γ2. This is the most abundant $GABA_A$ receptor subtype, and is believed to represent almost half of all $GABA_A$ receptors in the brain.

Two other major populations are the α2βγ2 and α3βγ2/3 subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at α1βγ2, α2βγ2 or α3βγ2 subtypes will possess desirable anxiolytic properties. Compounds which are modulators of the benzodiazepine binding site of the $GABA_A$ receptor by acting as BZ agonists are referred to hereinafter as "$GABA_A$ receptor agonists". The α1-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the α1 subunit. Accordingly, it is considered that $GABA_A$ receptor agonists which interact more favourably with the α2 and/or α3 subunit than with α1 will be effective in the treatment of anxiety with a reduced propensity to cause sedation. Moreover, agents which are inverse agonists of the α5 subunit are likely to be beneficial in enhancing cognition, for example in subjects suffering from dementing conditions such as Alzheimer's disease. Also, agents which are antagonists or inverse agonists at α1 might be employed to reverse sedation or hypnosis caused by α1 agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; Tourette's syndrome; speech disorders, including stuttering; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic patients; hearing disorders, including tinnitus and age-related hearing impairment; urinary incontinence; and the effects of substance abuse or dependency, including alcohol withdrawal. Selective ligands for $GABA_A$ receptors may be beneficial in enhancing cognition, for example in subjects suffering from dementing conditions such as Alzheimer's disease; and may also be effective as pre-medication prior to anaesthesia or minor procedures such as endoscopy, including gastric endoscopy.

In addition, the compounds in accordance with the present invention may be useful as radioligands in assays for detecting compounds capable of binding to the human $GABA_A$ receptor.

The present invention provides a class of triazine derivatives which possess desirable binding properties at various $GABA_A$ receptor subtypes. The compounds in accordance with the present invention have good affinity as ligands for the α2 and/or α3 and/or α5 subunit of the human $GABA_A$ receptor. The compounds of this invention may interact more favourably with the α2 and/or α3 subunit than with the α1 subunit; and/or may interact more favourably with the α5 subunit than with the α1 subunit.

The compounds of the present invention are $GABA_A$ receptor subtype ligands having a binding affinity ($K_i$) for the α2 and/or α3 and/or α5 subunit, as measured in the assay described hereinbelow, of 200 nM or less, typically of 100 nM or less, and ideally of 20 nM or less. The compounds in accordance with this invention may possess at least a 2-fold, suitably at least a 5-fold, and advantageously at least a 10-fold, selective affinity for the α2 and/or α3 and/or α5 subunit relative to the α1 subunit. However, compounds which are not selective in terms of their binding affinity for the α2 and/or α3 and/or α5 subunit relative to the α1 subunit are also encompassed within the scope of the present invention; such compounds will desirably exhibit functional selectivity in terms of zero or weak (positive or negative) efficacy at the α1 subunit and (i) a full or partial agonist profile at the α2 and/or α3 subunit, and/or (ii) an inverse agonist profile at the α5 subunit.

The present invention provides a compound of formula I, or an N-oxide thereof or a pharmaceutically acceptable salt thereof:

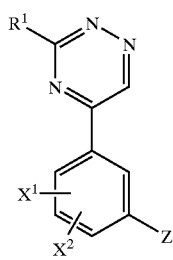

(I)

wherein $X^1$ represents hydrogen, halogen, $C_{1-6}$ alkyl, trifluoromethyl or $C_{1-6}$ alkoxy;

$X^2$ represents hydrogen or halogen;

Z represents hydrogen, halogen, cyano, cyanomethyl, trifluoromethyl, nitro, hydroxy, hydroxy($C_{1-6}$)alkyl, $C_{1-6}$ alkoxy, $C_{1-6}$ alkoxy($C_{1-6}$)alkyl, trifluoromethoxy, trifluoromethylthio, trifluoromethanesulfinyl, formyl, $C_{2-6}$ alkoxycarbonyl, oxopyrrolidinyl, or an optionally substituted aryl, heteroaryl or heteroaryl($C_{1-6}$)alkoxy group; and $R^1$ represents aryl or heteroaryl, either of which groups may be optionally substituted.

Where Z or $R^1$ in the compounds of formula I above represents aryl or heteroaryl, or (in the case of group Z) heteroaryl($C_{1-6}$)alkoxy, this group may be unsubstituted, or substituted by one or more substituents. Typically, the group Z or $R^1$ will be unsubstituted, or substituted by one or two substituents. Typical substituents on the group Z or $R^1$ include halogen, cyano, trifluoromethyl, nitro, $C_{1-6}$ alkyl, hydroxy, $C_{1-6}$ alkoxy, oxy, $C_{1-6}$ alkylsulphonyl, amino, aminocarbonyl, formyl and $C_{2-6}$ alkoxycarbonyl. Illustrative substituents on Z or $R^1$ include halogen, cyano, trifluoromethyl, $C_{1-6}$ alkoxy and aminocarbonyl.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl, isobutyl, tert-butyl and 2,2-dimethylpropyl. Derived expressions such as "$C_{1-6}$ alkoxy", "$C_{1-6}$ alkylamino" and "$C_{1-6}$ alkylsulphonyl" are to be construed accordingly.

Typical aryl groups include phenyl and naphthyl, preferably phenyl.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkoxy" as used herein includes furylmethoxy, furylethoxy, thienylmethoxy, thienylethoxy, pyrazolylmethoxy, oxazolylmethoxy, oxazolylethoxy, thiazolylmethoxy, thiazolylethoxy, imidazolylmethoxy, imidazolylethoxy, oxadiazolylmethoxy, oxadiazolylethoxy, thiadiazolylmethoxy, thiadiazolylethoxy, triazolylmethoxy, triazolylethoxy, tetrazolylmethoxy, tetrazolylethoxy, pyridinylmethoxy, pyridinylethoxy, pyrimidinylmethoxy, pyrazinylmethoxy, quinolinylmethoxy and isoquinolinylmethoxy.

The term "halogen" as used herein includes fluorine, chlorine, bromine and iodine, especially fluoro or chloro.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitable values for the $X^1$ substituent include hydrogen, fluoro, chloro, methyl, trifluoromethyl and methoxy; in particular hydrogen or fluoro; and especially fluoro.

Typical values of $X^2$ include hydrogen and fluoro, especially hydrogen.

Typically, Z represents an optionally substituted aryl or heteroaryl group.

Selected values for the substituent Z include phenyl, pyridinyl, pyridazinyl, pyrimidinyl, pyrazinyl, furyl, thienyl, oxazolyl, isoxazolyl, thiazolyl, isothiazolyl, pyrrolyl, pyrazolyl, imidazolyl, oxadiazolyl, thiadiazolyl, triazolyl and tetrazolyl, any of which groups may be optionally substituted by one or more substituents.

In one favoured embodiment, Z represents an optionally substituted phenyl group, in particular monosubstituted or disubstituted phenyl. In another favoured embodiment, Z represents optionally substituted pyridinyl, especially unsubstituted, monosubstituted or disubstituted pyridin-2-yl, pyridin-3-yl or pyridin-4-yl.

Examples of suitable substituents on the group Z include fluoro, chloro, cyano, trifluoromethyl, nitro, methyl, hydroxy, methoxy, oxy, methanesulphonyl, amino, aminocarbonyl, formyl and methoxycarbonyl.

Examples of particular substituents on the group Z include fluoro, cyano, trifluoromethyl and aminocarbonyl, especially fluoro or cyano.

Detailed values of Z include fluorophenyl, cyanophenyl, (cyano)(fluoro)phenyl, (chloro)(cyano)phenyl, trifluoromethyl-phenyl, nitrophenyl, methoxyphenyl, methanesulphonyl-phenyl, pyridinyl, fluoro-pyridinyl, difluoro-pyridinyl, (amino)(chloro)pyridinyl, cyano-pyridinyl, methyl-pyridinyl, hydroxy-pyridinyl, methoxy-pyridinyl, oxy-pyridinyl, aminocarbonyl-pyridinyl, pyridazinyl, pyrimidinyl, pyrazinyl, cyano-thienyl, aminocarbonyl-thienyl, formyl-thienyl, methoxycarbonyl-thienyl, thiazolyl, isothiazolyl, pyrrolyl, pyrazolyl, imidazolyl, triazolyl and methyl-tetrazolyl.

Particular values of Z include fluorophenyl, cyanophenyl, (cyano)(fluoro)phenyl, trifluoromethyl-phenyl, fluoro-pyridinyl and difluoro-pyridinyl.

Typical values of Z include hydrogen, fluoro, bromo, cyano, cyanomethyl, trifluoromethyl, nitro, hydroxy, hydroxypropyl (especially 2-hydroxyprop-2-yl), methoxy, methoxypropyl (especially 2-methoxyprop-2-yl), trifluoromethoxy, trifluoromethylthio, trifluoromethanesulfinyl, isopropoxy, formyl, methoxycarbonyl, oxopyrrolidinyl, fluorophenyl, cyanophenyl, (cyano)(fluoro)phenyl, trifluoromethyl-phenyl, pyridinyl, fluoro-pyridinyl, difluoro-pyridinyl, triazolyl, (methyl)(trifluoromethyl)-pyrazolyl-methoxy, methyltriazolyl-methoxy and pyridinyl-methoxy.

Illustrative values of Z include bromo, trifluoromethyl, hydroxypropyl (especially 2-hydroxyprop-2-yl), methoxypropyl (especially 2-methoxyprop-2-yl), trifluoromethoxy, trifluoromethylthio, trifluoromethylsulfinyl, 2-oxopyrrolidin-1-yl, fluorophenyl, cyanophenyl, (cyano)(fluoro)phenyl, trifluoromethyl-phenyl, fluoro-pyridinyl and difluoro-pyridinyl.

In one embodiment, Z represents fluoro-pyridinyl. In another embodiment, Z represents difluoro-pyridinyl.

Typically, $R^1$ represents phenyl, pyridinyl, pyrazinyl, furyl, thienyl, thiazolyl or triazolyl, any of which groups may be optionally substituted by one or more substituents.

Suitably, $R^1$ represents phenyl or pyridinyl, either of which groups may be optionally substituted by one or more substituents.

Examples of typical substituents on $R^1$ include halogen, $C_{1-6}$ alkyl, trifluoromethyl, $C_{1-6}$ alkoxy and cyano. Suitable substituents on $R^1$ include fluoro, chloro, methyl, trifluoromethyl, methoxy and cyano; in particular fluoro or methoxy; and especially fluoro.

Individual values of $R^1$ include phenyl, fluorophenyl, chlorophenyl, difluorophenyl, (chloro)(fluoro)phenyl, (fluoro)(methyl)phenyl, (fluoro)(trifluoromethyl)phenyl, methoxyphenyl, (fluoro)(methoxy)phenyl, cyanophenyl, (cyano)(fluoro)phenyl, pyridinyl, fluoro-pyridinyl, difluoro-pyridinyl, pyrazinyl, furyl, thienyl, thiazolyl and triazolyl.

Representative values of $R^1$ include phenyl, fluorophenyl, difluorophenyl, (chloro)(fluoro)phenyl, methoxyphenyl, pyridinyl, fluoro-pyridinyl and difluoro-pyridinyl.

Illustrative values of $R^1$ include phenyl, fluorophenyl, difluorophenyl, methoxyphenyl, pyridinyl and fluoro-pyridinyl.

A particular sub-class of compounds according to the invention is represented by the compounds of formula IIA, and N-oxides thereof and pharmaceutically acceptable salts thereof:

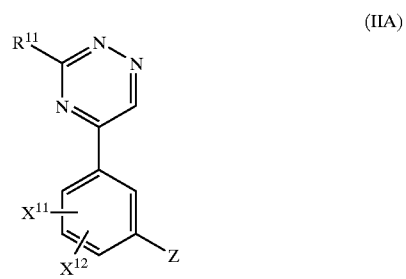

(IIA)

wherein

Z is as defined above;

$X^{11}$ represents hydrogen, fluoro, chloro, methyl, trifluoromethyl or methoxy;

$X^{12}$ represents hydrogen or fluoro; and $R^{11}$ represents phenyl, pyridinyl, pyrazinyl, furyl, thienyl, thiazolyl or triazolyl, any of which groups may be optionally substituted by one or more substituents selected from halogen, $C_{1-6}$ alkyl, trifluoromethyl, $C_{1-6}$ alkoxy and cyano.

Suitable values of $X^{11}$ include hydrogen and fluoro, especially fluoro.

In a favoured embodiment; $X^{12}$ represents hydrogen. In another embodiment, $X^{12}$ represents fluoro.

Suitably, $R^{11}$ represents an optionally substituted phenyl or pyridinyl group.

Suitable substituents on $R^{11}$ include fluoro, chloro, methyl, trifluoromethyl, methoxy and cyano. Particular substituents include fluoro and methoxy, especially fluoro.

Individual values of $R^{11}$ include phenyl, fluorophenyl, chlorophenyl, difluorophenyl, (chloro)(fluoro)phenyl, (fluoro)(methyl)phenyl, (fluoro)(trifluoromethyl)phenyl, methoxyphenyl, (fluoro)(methoxy)phenyl, cyanophenyl, (cyano)(fluoro)phenyl, pyridinyl, fluoro-pyridinyl, difluoro-pyridinyl, pyrazinyl, furyl, thienyl, thiazolyl and triazolyl.

Representative values of $R^{11}$ include phenyl, fluorophenyl, difluorophenyl, (chloro)(fluoro)phenyl, methoxyphenyl, pyridinyl, fluoro-pyridinyl and difluoro-pyridinyl.

Illustrative values of $R^{11}$ include phenyl, fluorophenyl, difluorophenyl, methoxyphenyl, pyridinyl and fluoro-pyridinyl.

One representative subset of the compounds of formula IIA above is represented by the compounds of formula IIB, and N-oxides thereof and pharmaceutically acceptable salts thereof:

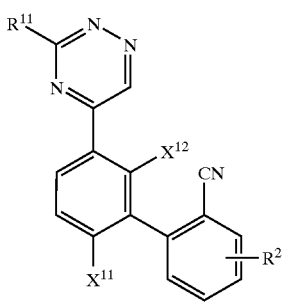

(IIB)

wherein $X^{11}$, $X^{12}$ and $R^{11}$ are as defined above; and
$R^2$ represents hydrogen or fluoro.

In one embodiment, $R^2$ is hydrogen.

In another embodiment, $R^2$ is fluoro, in which case the fluorine atom $R^2$ is favourably attached to the phenyl ring at the 4-, 5- or 6-position (relative to the cyano group at position 2).

Another representative subset of the compounds of formula IIA above is represented by the compounds of formula IIC, and N-oxides thereof and pharmaceutically acceptable salts thereof:

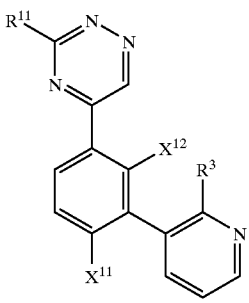

(IIC)

wherein $X^{11}$, $X^{12}$ and $R^{11}$ are as defined above; and
R3 represents hydrogen, fluoro, cyano or methyl.

In one embodiment, $R^3$ is hydrogen.

In an additional embodiment, $R^3$ is fluoro.

In another embodiment, $R^3$ is cyano.

In a further embodiment, $R^3$ is methyl.

A further representative subset of the compounds of formula IIA above is represented by the compounds of formula IID, and N-oxides thereof and pharmaceutically acceptable salts thereof:

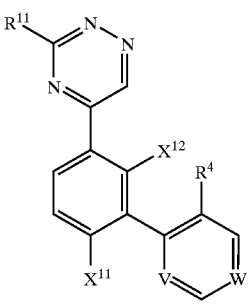

(IID)

wherein $X^{11}$, $X^{12}$ and $R^{11}$ are as defined above;
V represents N and W represents CH or CF; or
V represents CH or CF and W represents N; and
$R^4$ represents hydrogen or fluoro.

In one embodiment, V is N and W is CH.
In another embodiment, V is N and W is CF.
In an alternative embodiment, V is CH and W is N.
In a further embodiment, V is CF and W is N.
In a typical embodiment, $R^4$ represents hydrogen.
In another embodiment, $R^4$ represents fluoro.

Specific compounds within the scope of the present invention include:

2'-fluoro-5'-(3-phenyl-[1,2,4]triazin-5-yl)biphenyl-2-carbonitrile;
4,2'-difluoro-5'-[3-(4-fluorophenyl)-[1,2,4]triazin-5-yl]biphenyl-2-carbonitrile;
4,2'-difluoro-5'-[3-(2,4-difluorophenyl)-[1,2,4]triazin-5-yl]biphenyl-2-carbonitrile;
4,2'-difluoro-5'-[3-(2-fluorophenyl)-[1,2,4]triazin-5-yl]biphenyl-2-carbonitrile;
4,2'-difluoro-5'-[3-(4-methoxyphenyl)-[1,2,4]triazin-5-yl]biphenyl-2-carbonitrile;
3-(2,4-difluorophenyl)-5-[4-fluoro-3-(3-fluoropyridin-4-yl)phenyl]-[1,2,4]triazine;
5-[4-fluoro-3-(3-fluoropyridin-4-yl)phenyl]-3-(4-methoxyphenyl)-[1,2,4]triazine;
5-(3-bromo-4-fluorophenyl)-3-(2,4-difluorophenyl)-[1,2,4]triazine;
5-(3-bromo-4-fluorophenyl)-3-(4-methoxyphenyl)-[1,2,4]triazine;
5-[3-(3,5-difluoropyridin-4-yl)-4-fluorophenyl]-3-(2,4-difluorophenyl)-[1,2,4]triazine;
5-[3-(3,5-difluoropyridin-2-yl)-4-fluorophenyl]-3-(4-methoxyphenyl)-[1,2,4]triazine;
6,2'-difluoro-5'-[3-(2,4-difluorophenyl)-[1,2,4]triazin-5-yl]biphenyl-2-carbonitrile;
3-(2,4-difluorophenyl)-5-(2-fluoro-2'-trifluoromethylbiphenyl-5-yl)-[1,2,4]triazine;
5-(2,2'-difluorobiphenyl-5-yl)-3-(2,4-difluorophenyl)-[1,2,4]triazine;
5,2'-difluoro-5'-[3-(2,4-difluorophenyl)-[1,2,4]triazin-5-yl]biphenyl-2-carbonitrile;
3,2'-difluoro-5'-[3-(2,4-difluorophenyl)-[1,2,4]triazin-5-yl]biphenyl-2-carbonitrile;
5-[3-(2,4-difluorophenyl)-[1,2,4]triazin-5-yl]-2-fluorobenzonitrile;
3-(2-fluorophenyl)-5-[4-fluoro-3-(pyridin-3-yl)phenyl]-[1,2,4]triazine;
5-[4-fluoro-3-(pyridin-3-yl)phenyl]-3-(4-methoxyphenyl)-[1,2,4]triazine;
3-(2,4-difluorophenyl)-5-[4-fluoro-3-(pyridin-3-yl)phenyl]-[1,2,4]triazine;
5-[4-fluoro-3-(pyridin-2-yl)phenyl]-3-(pyridin-2-yl)-[1,2,4]triazine;
2-{5-[3-(2,4-difluorophenyl)-[1,2,4]triazin-5-yl]-2-fluorophenyl}propan-2-ol;
3-(2,4-difluorophenyl)-5-[4-fluoro-3-(1-methoxy-1-methylethyl)phenyl]-[1,2,4]triazine;
5-(4-fluoro-3-trifluoromethylphenyl)-3-(4-methoxyphenyl)-[1,2,4]triazine;
3-(4-methoxyphenyl)-5-(3-trifluoromethoxyphenyl)-[1,2,4]triazine;
3-(2,4-difluorophenyl)-5-(4-fluoro-3-trifluoromethylphenyl)-[1,2,4]triazine;
3-(2,4-difluorophenyl)-5-(3-trifluoromethoxyphenyl)-[1,2,4]triazine;
3-(2,4-difluorophenyl)-5-(3-trifluoromethylsulfanylphenyl)-[1,2,4]triazine;
3-(4-methoxyphenyl)-5-(3-trifluoromethylsulfanylphenyl)-[1,2,4]triazine;

1-{3-[3-(2,4-difluorophenyl)-[1,2,4]triazin-5-yl]
phenyl}pyrrolidin-2-one;
1-{3-[3-(4-methoxyphenyl)-[1,2,4]triazin-5-yl]
phenyl}pyrrolidin-2-one;
3-(2,4-difluorophenyl)-5-(3-
trifluoromethanesulfinylphenyl)-[1,2,4]triazine 1-oxide;
5'-[3-(2,4-difluorophenyl)-[1,2,4]triazin-5-yl]-2'-
fluorobiphenyl-4-carbonitrile;
3-(2,4-difluorophenyl)-5-[4-fluoro-3-(3-fluoropyridin-2-yl)
phenyl]-[1,2,4]triazine;
5-[4-fluoro-3-(3-fluoropyridin-2-yl)phenyl]-3-(4-
methoxyphenyl)-[1,2,4]triazine;
5-[4-fluoro-3-(3-fluoropyridin-2-yl)phenyl]-3-(3-
fluoropyridin-4-yl)-[1,2,4]triazine;
3-(2,4-difluorophenyl)-5-(4-fluoro-3-
trifluoromethylphenyl)-[1,2,4]triazine 1-oxide;
5-[4-fluoro-3-(3-fluoropyridin-2-yl)phenyl]-3-(3-
fluoropyridin-2-yl)-[1,2,4]triazine;
3-(3,5-difluoropyridin-2-yl)-5-[3-(3,5-difluoropyridin-2-
yl)-4-fluorophenyl]-[1,2,4]triazine;
3-(4-chloro-2-fluorophenyl)-5-[4-fluoro-3-(3-fluoropyridin-
2-yl)phenyl]-[1,2,4]triazine;
3-(3,5-difluoropyridin-2-yl)-5-[4-fluoro-3-(3-fluoropyridin-
2-yl)phenyl]-[1,2,4]triazine;
and pharmaceutically acceptable salts thereof.

Also provided by the present invention is a method for the treatment and/or prevention of anxiety which comprises administering to a patient in need of such treatment an effective amount of a compound of formula I as defined above or a pharmaceutically acceptable salt thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the anxiolytic compounds of the invention is ideally 50 nM or less, preferably 10 nM or less, and more preferably 5 nM or less.

The anxiolytic compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds according to the present invention may exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are likely to be substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In another aspect, the present invention provides a method for the treatment and/or prevention of cognitive disorders, including dementing conditions such as Alzheimer's disease, which comprises administering to a patient in need of such treatment an effective amount of a compound of formula I as defined above or a pharmaceutically acceptable salt thereof.

Cognition enhancement can be shown by testing the compounds in the Morris watermaze as reported by McNamara and Skelton, *Psychobiology*, 1993, 21, 101–108. Further details of relevant methodology are described in WO 96/25948.

Cognitive disorders for which the compounds of the present invention may be of benefit include delirium, dementia, amnestic disorders, and cognition deficits, including age-related memory deficits, due to traumatic injury, stroke, Parkinson's disease and Down Syndrome. Any of these conditions may be attributable to substance abuse or withdrawal. Examples of dementia include dementia of the Alzheimer's type with early or late onset, and vascular dementia, any of which may be uncomplicated or accompanied by delirium, delusions or depressed mood; and dementia due to HIV disease, head trauma, Parkinson's disease or Creutzfeld-Jakob disease.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of neurological disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

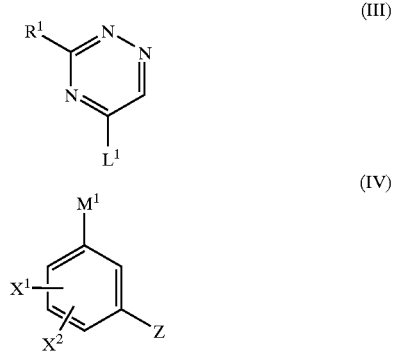

wherein $X^1$, $X^2$, Z and $R^1$ are as defined above, $L^1$ represents a suitable leaving group, and $M^1$ represents a boronic acid moiety —$B(OH)_2$ or a cyclic ester thereof formed with an organic diol, e.g. pinacol, 1,3-propanediol or neopentyl glycol, or $M^1$ represents —$Sn(Alk)_3$ in which Alk represents a $C_{1-6}$ alkyl group, typically n-butyl; in the presence of a transition metal catalyst.

The leaving group $L^1$ is typically a halogen atom, e.g. iodo, bromo or chloro.

The transition metal catalyst of use in the reaction between compounds III and IV is suitably tetrakis (triphenylphosphine)-palladium(0). The reaction is conveniently carried out at an elevated temperature in a solvent such as N,N-dimethylacetamide, 1,4-dioxane or tetrahydrofuran, advantageously in the presence of one or more substances selected from potassium phosphate, copper (I) iodide, lithium chloride, sodium carbonate, cesium carbonate and copper(I) 3-methylsalicylate. Alternatively, the transition metal catalyst employed may be dichloro[1,1'-bis(diphenylphosphino)ferrocene]palladium(II), in which case the reaction is conveniently effected at an elevated temperature in a solvent such as N,N-dimethylformamide, advantageously in the presence of potassium phosphate.

In an alternative procedure, the compounds according to the present invention may be prepared by a process which comprises reacting a compound of formula V with a compound of formula VI:

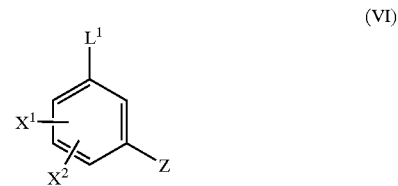

wherein $X^1$, $X^2$, $Z^1$, $R^1$, $L^1$ and $M^1$ are as defined above; in the presence of a transition metal catalyst; under conditions analogous to those described above for the reaction between compounds III and IV.

In another procedure, the compounds according to the present invention may be prepared by a process which comprises reacting a compound of formula VII with a compound of formula VIII:

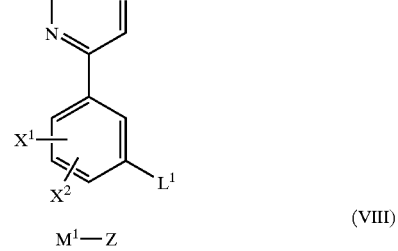

wherein $X^1$, $X^2$, Z, $R^1$, $L^1$ and $M^1$ are as defined above; in the presence of a transition metal catalyst; under conditions analogous to those described above for the reaction between compounds III and IV.

In the compounds of formula VI and VII above, the leaving group $L^1$ is typically trifluoromethanesulfonyloxy (triflyloxy); or a halogen atom, e.g. bromo.

Alternatively, the compounds according to the present invention may be prepared by a process which comprises reacting a compound of formula IX with a compound of formula X:

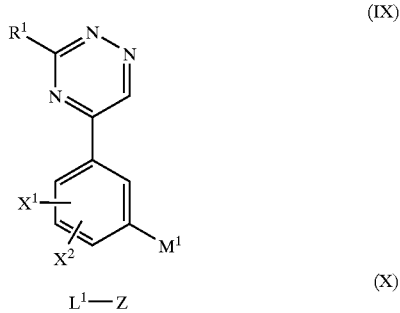

(IX)

(X)

L¹—Z wherein X¹, X², Z, R¹, L¹ and M¹ are as defined above; in the presence of a transition metal catalyst; under conditions analogous to those described above for the reaction between compounds III and IV.

In an additional procedure, the compounds according to the present invention in which Z represents $C_{1-6}$ alkoxy or optionally substituted heteroaryl($C_{1-6}$)alkoxy may be prepared by a process which comprises reacting a compound of formula XI with a compound of formula XII:

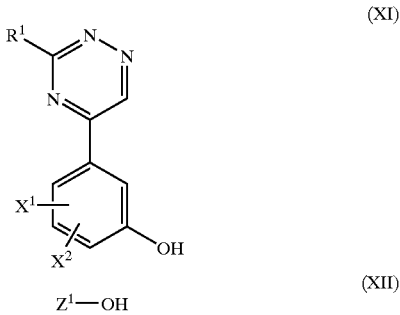

(XI)

(XII)

Z¹—OH wherein X¹, X² and R¹ are as defined above, and Z¹ represents $C_{1-6}$ alkyl or optionally substituted heteroaryl($C_{1-6}$)alkyl; in the presence of triphenylphosphine and a dialkyl azodicarboxylate, e.g. diisopropyl azodicarboxylate (DIAD) or diethyl azodicarboxylate (DEAD).

The reaction is conveniently carried out by stirring in a solvent such as tetrahydrofuran.

Where M¹ in the intermediates of formula IV and IX above represents a boronic acid moiety —B(OH)₂ or a cyclic ester thereof formed with pinacol or neopentyl glycol, the relevant compound IV or IX may be prepared by reacting bis(pinacolato)diboron or bis(neopentyl glycolato)diborane respectively with a compound of formula VI or VII as defined above; in the presence of a transition metal catalyst.

The transition metal catalyst of use in the reaction between bis(pinacolato)diboron or bis(neopentyl glycolato) diborane and compound VI or VII is suitably dichloro[1,1'-bis(diphenylphosphino)ferrocene]-palladium(II). The reaction is conveniently carried out at an elevated temperature in a solvent such as 1,4-dioxane, optionally in admixture with dimethylsulfoxide, typically in the presence of 1,1'-bis(diphenylphosphino)ferrocene and/or potassium acetate.

Where L¹ in the intermediates of formula VII above represents triflyloxy, the relevant compound VII may be prepared by reacting the appropriate compound of formula XI as defined above with triflic anhydride, typically in the presence of pyridine. Analogous conditions may be utilised for preparing a compound of formula VI wherein L¹ represents triflyloxy from the corresponding hydroxy precursor.

The intermediates of formula XI above may suitably be prepared from the appropriate methoxy-substituted precursor of formula XIII:

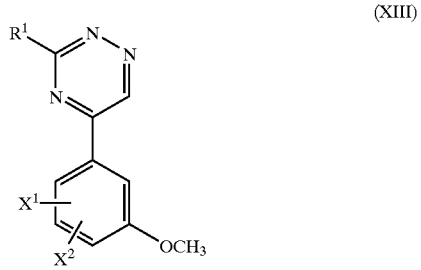

(XIII)

wherein X¹, X² and R¹ are as defined above; by treatment with boron tribromide, typically in chloroform or dichloromethane; or with hydrogen bromide, typically in acetic acid at reflux.

Where M¹ in the intermediates of formula V above represents —Sn(Alk)₃ and Alk is as defined above, this compound may be prepared by reacting a compound of formula III as defined above with a reagent of formula (Alk)₃Sn-Hal, in which Hal represents a halogen atom, typically chloro. The reaction is conveniently effected by treating compound III with isopropylmagnesium chloride, typically in a solvent such as tetrahydrofuran, with subsequent addition of the stannyl reagent (Alk)₃Sn-Hal.

In a further procedure, the compounds according to the present invention may be prepared by a process which comprises reacting a compound of formula XIV with a compound of formula XV:

R¹—M¹ (XIV)

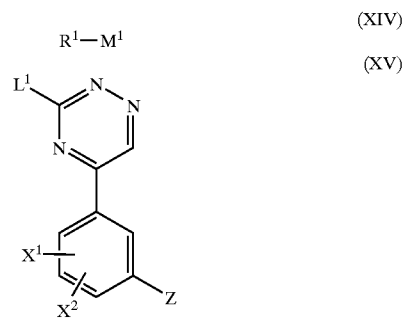

(XV)

wherein X¹, X², Z, R¹, L¹ and M¹ are as defined above; in the presence of a transition metal catalyst; under conditions analogous to those described above for the reaction between compounds III and IV.

In the compounds of formula XV above, the leaving group L¹ is typically methylthio; a sulfonyloxy group such as triflyloxy; or a halogen atom, e.g. chloro. Preferably, L¹ in compound XV represents methylthio.

In a still further procedure, the compounds according to the present invention may be prepared by a process which comprises reacting a compound of formula XVI with a compound of formula XVII:

R¹—L¹ (XVI)

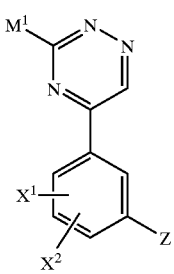

(XVII)

wherein $X^1$, $X^2$, Z, $R^1$, $L^1$ and $M^1$ are as defined above; in the presence of a transition metal catalyst; under conditions analogous to those described above for the reaction between compounds III and IV.

The intermediates of formula XVII wherein $M^1$ represents —Sn(Alk)$_3$ and Alk represents $C_{1-6}$ alkyl, e.g. methyl, may be prepared by reacting a compound of formula XV as defined above with a reagent of formula (Alk)$_3$Sn—Sn(Alk)$_3$. The reaction is conveniently effected in the presence of a transition metal catalyst, e.g. tetrakis(triphenylphosphine)palladium(0), with heating in a solvent such as 1,4-dioxane, typically in the presence of lithium chloride.

In a yet further procedure, the compounds according to the present invention wherein $R^1$ represents 1H-[1,2,3]triazol-4-yl may be prepared by a process which comprises reacting a compound of formula XVIII:

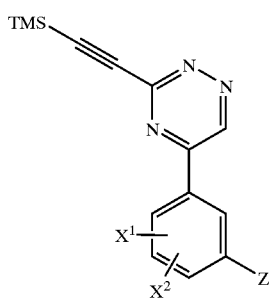

(XVIII)

wherein $X^1$, $X^2$ and Z are as defined above, and TMS is an abbreviation for trimethylsilanyl; with sodium azide.

The reaction is conveniently effected by stirring the reactants in a solvent such as N,N-dimethylformamide.

The intermediates of formula XVIII may be prepared by reacting a compound of formula XV with TMS-acetylene, in the presence of a transition metal catalyst such as bis(triphenylphosphine)palladium(II) chloride. The reaction is conveniently effected by stirring in a solvent such as tetrahydrofuran, typically in the presence of triethylamine, triphenylphosphine and copper(I) chloride.

The compounds according to the present invention wherein Z represents cyano may be prepared by a process which comprises reacting a compound of formula VII above wherein $L^1$ represents a halogen atom, e.g. bromo, with zinc cyanide; in the presence of a transition metal catalyst.

The transition metal catalyst of use in the foregoing reaction is ideally tetrakis(triphenylphosphine)palladium(0), in which case the reaction is conveniently effected at an elevated temperature in a solvent such as N,N-dimethylformamide.

The compounds in accordance with the present invention may also be prepared by a process which comprises reacting a compound of formula XIX with a compound of formula XX:

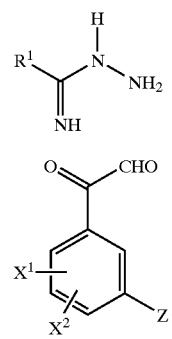

(XIX)

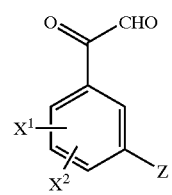

(XX)

wherein $X^1$, $X^2$, Z and $R^1$ are as defined above.

The reaction is conveniently carried out by stirring the reactants, typically at an elevated temperature, in a solvent such as aqueous ethanol, optionally in the presence of sodium hydrogencarbonate.

The intermediates of formula XIX may be prepared by reacting a compound of formula XXI:

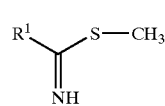

(XXI)

wherein $R^1$ is as defined above; with hydrazine, typically in tetrahydrofuran, optionally in admixture with methanol.

The intermediates of formula XXI may be prepared by reacting a compound of formula XXII:

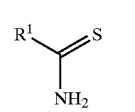

(XXI)

wherein $R^1$ is as defined above; with a methylating agent.

The methylating agent is suitably methyl iodide, in which case the reaction is conveniently carried out in a solvent such as acetone, typically at an elevated temperature.

The intermediates of formula XX may be prepared by reacting a compound of formula XXIII:

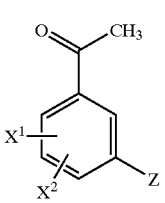

(XXIII)

wherein $X^1$, $X^2$ and Z are as defined above; with selenium dioxide, typically at an elevated temperature in aqueous 1,4-dioxane.

Where $L^1$ in compound XV represents methylthio, the relevant compound may be prepared by reacting a compound of formula XX as defined above with the compound of formula XXIV:

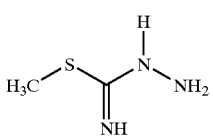
(XXIV)

under conditions analogous to those described above for the reaction between compounds XIX and XX.

The intermediates of formula XV above wherein $L^1$ represents methylthio are novel compounds in their own right, and represent a further feature of the present invention.

The compounds of formula XI and XIII above correspond to compounds of formula I as defined above wherein Z represents hydroxy and methoxy respectively, and they may therefore be prepared by any of the methods described above for the preparation of the compounds according to the invention. Moreover, where $L^1$ in compound VII above represents a halogen atom, these compounds correspond to compounds of formula I as defined above, and they therefore constitute compounds in accordance with the invention in their own right.

Where they are not commercially available, the starting materials of formula III, VIII, X, XII, XIV, XVI, XXII and XXIII may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I initially obtained may be converted into the N-oxide derivative thereof by treatment with m-chloroperbenzoic acid. Similarly, a compound of formula I wherein Z represents trifluoromethylthio initially obtained may be converted into the corresponding compound wherein Z represents trifluoromethylsulfinyl by treatment with m-chloroperbenzoic acid. A compound of formula I wherein Z represents bromo initially obtained may be converted into the corresponding compound wherein Z represents acetyl by treatment with tributyl(1-ethoxyvinyl) tin in the presence of a transition metal catalyst such as tetrakis(triphenylphosphine)palladium(0). A compound of formula I wherein Z is acetyl may be converted into the corresponding compound wherein Z represents 2-hydroxyprop-2-yl by treatment with a Grignard reagent such as methylmagnesium chloride; and the resulting product may in turn be converted into the corresponding compound wherein Z represents 2-methoxyprop-2-yl by treatment with a methylating agent such as methyl iodide. A compound of formula I wherein Z is substituted with methoxy may be converted into the corresponding compound wherein Z is substituted with hydroxy by treatment with boron tribromide.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α2 and/or α3 and/or α5 subunit stably expressed in Ltk$^-$ cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM; for α5β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 and/or α5 subunit of the human GABA$_A$ receptor of 100 nM or less.

EXAMPLE 1

2'-Fluoro-5'-(3-phenyl-[1,2,4]triazin-5-yl)biphenyl-2-carbonitrile 1-(3-Chloro-4-fluorophenyl)ethanone (0.86 g, 5.0 mmol), 2-(4,4,5,5-tetramethyl[1,3,2]dioxaborolan-2-yl)benzonitrile (1.37 g, 6.0 mmol) (prepared according to the procedure described in WO 02/74773) and potassium fluoride (0.96 g, 16.5 mmol) were suspended in tetrahydrofuran (20 ml) and the mixture degassed with nitrogen for 30 min. Tris(dibenzylidineacetone)dipalladium(0) (0.14 g, 0.15 mmol) and tri-tert-butylphosphine (0.3M in 1,4-dioxane, 1.0 ml) were added and the mixture stirred at room temperature for 1 h then heated at 50° C. for 18 h. The mixture was allowed to cool to room temperature and then poured into 0.5N sodium hydroxide solution (300 ml) and stirred for 30 min. The solid was filtered, washed with water (50 ml) and isohexane (50 ml) and the brown solid left to air-dry. The solid was purified by flash column chromatography on silica eluting with isohexane on a gradient of ethyl acetate (10–30%). Collecting the appropriate fractions gave 5'-acetyl-2'-fluorobiphenyl-2-carbonitrile (0.31 g, 26%) as a yellow solid: $\delta_H$(400 MHz, CDCl$_3$) 2.64 (3H, s), 7.31 (1H, t, J 8.8 Hz), 7.52–7.56 (2H, m), 7.68–7.72 (1H, m), 7.81 (1H, dd, J 0.8, 7.4 Hz), 8.04–8.09 (2H, m).

5'-Acetyl-2'-fluorobiphenyl-2-carbonitrile (0.31 g, 1.3 mmol) was suspended in 1,4-dioxane (4.75 ml) and water (0.25 ml) and warmed to 60° C. to solubilise the starting material. The solution was then cooled to ambient temperature, selenium dioxide (0.17 g, 1.55 mmol) added and the mixture heated under reflux for 2 h. The mixture was then allowed to cool to 60° C., activated charcoal (1 g) added and the mixture stirred for 30 min. The mixture was then allowed to cool to ambient temperature, filtered through a glass fibre filter paper and the solid washed with 1,4-dioxane (10 ml) and the filtrate evaporated to give crude 2'-fluoro-5'-(2-oxoacetyl)biphenyl-2-carbonitrile which was used without further purification in the next step.

2'-Fluoro-5'-(2-oxoacetyl)biphenyl-2-carbonitrile (0.34 g, 1.3 mmol) and benzimidrazone (0.33 g, 1.3 mmol) were dissolved in ethanol (8 ml) and water (2 ml) and stirred at room temperature for 15 min then heated under reflux for 2 h. The mixture was allowed to cool to ambient temperature then the solvent was evaporated. The residue was partitioned between ethyl acetate (100 ml) and water (50 ml) with saturated sodium hydrogencarbonate solution (10 ml). The organic phase was washed with brine (30 ml), dried over anhydrous sodium sulfate, filtered and evaporated to give an orange oil. The oil was purified by flash column chromatography on silica eluting with isohexane on a gradient of ethyl acetate (15–25%). Collecting appropriate fractions followed by trituration with diethyl ether/isohexane (1:1, 5 ml) gave 2'-fluoro-5'-(3-phenyl-[1,2,4]triazin-5-yl)biphenyl-2-carbonitrile (13 mg, 3%) as a pale yellow solid: $\delta_H$(360 MHz, CDCl$_3$) 7.47 (1H, t, J 9.3 Hz), 7.56–7.60 (4H, m), 7.61 (1H, d, J 7.4 Hz), 7.75 (1H, t, J 7.5 Hz), 7.86 (1H, d, J 7.7 Hz), 8.38–8.40 (2H, m), 8.63–8.66 (2H, m), 9.63 (1H, s); m/z (ES$^+$) 353 (M$^+$+H).

EXAMPLE 2

4,2'-Difluoro-5'-[3-(4-fluorophenyl)-[1,2,4]triazin-5-yl]biphenyl-2-carbonitrile 1-[4-Fluoro-3-(4,4,5,5-tetramethyl-[1,3,2]dioxaborolan-2-yl)phenyl]ethanone To a solution of 3-bromo-4-fluoroacetophenone (10 g, 46.07 mmol) and bis(pinacolato)diboron (12.87 g, 50.68 mmol) in 1,4-dioxane (90 ml) and DMSO (10 ml) was added potassium acetate (9.04 g, 92.14 mmol) and the mixture degassed for 1 h. Dichloro[1,1'-bis(diphenylphosphino)-ferrocene]palladium(II) dichloromethane (DCM) adduct (1.13 g, 1.38 mmol) was added and the mixture degassed for a further 15 min and then heated at 90° C. for 18 h. After cooling to ambient temperature the mixture was filtered and the filter cake washed with ethyl acetate (2×50 ml). The filtrate was then washed with water (100 ml), brine (100 ml), dried (MgSO$_4$), filtered and evaporated to give the title product as a brown oil which was used without further purification (12.0 g): $\delta_H$ (400 MHz, CDCl$_3$) 1.38 (12H, s), 2.61 (2H, s), 2.61 (3H, s), 7.10 (1H, t, J 8.6 Hz), 8.05–8.09 (1H, m), 8.35 (1H, dd, J 2.3, 5.5 Hz).

5'-Acetyl-4,2'-difluorobiphenyl-2-carbonitrile

To a degassed solution of 1-[4-fluoro-3-(4,4,5,5-tetramethyl-[1,3,2]dioxaborolan-2-yl)phenyl]ethanone (12 g, 45.43 mmol), 2-bromo-5-fluorobenzonitrile (9.09 g, 5.28 ml, 45.44 mmol), potassium fluoride (7.92 g, 136.31 mmol) and tris(dibenzylideneacetone)palladium(0) (0.834 g, 0.908 mmol) in THF (200 ml) and water (10 ml) was added tri-tert butylphosphine (10% weight solution) (0.368 g, 3.63 ml, 1.817 mmol). The reaction was heated at 70° C. for 14 h then allowed to cool to ambient temperature. The reaction was partitioned between water (200 ml) and ether (300 ml). The aqueous phase was extracted with ether (150 ml) and the combined organics washed with brine (200 ml), dried (MgSO$_4$), filtered and evaporated to give a brown solid. The solid was dissolved in DCM and adsorbed onto silica. The crude product was chromatographed on silica (5–20% EtOAc in isohexane) to give the title product as a white solid (6.8 g): $\delta_H$ (400 MHz, CDCl$_3$) 2.63 (3H, s), 7.31 (1H, t, J 9.0 Hz), 7.40–7.44 (1H, m), 7.50–7.53 (2H, m), 8.02–8.10 (2H, m).

4,2'-Difluoro-5'-(2-oxoacetyl)biphenyl-2-carbonitrile

Selenium dioxide (0.556 g, 5.00 mmol) dissolved in 1,4dioxane:water (4:1, 5 ml) was added in one portion to 5'-acetyl-4,2'-difluorobiphenyl-2-carbonitrile (0.92 g, 3.58 mmol) in 1,4-dioxane (10 ml) and the mixture heated at reflux for 18 h. The reaction was allowed to cool to room temperature, filtered and the filtrate evaporated to give an orange-coloured glassy solid which was used without further purification (0.97 g).

4,2'-Difluoro-5'-(3-methylsulfanyl-[1,2,4]triazin-5-yl)biphenyl-2-carbonitrile

To a solution of methylthiosemicarbazide hydrogen iodide (0.459 g, 1.967 mmol) and sodium hydrogencarbonate (0.165 g, 1.967 mmol) in ethanol/water (10 ml, 4:1) was added a solution of 4,2'-diffluoro-5'-(2-oxoacetyl)biphenyl-2-carbonitrile (0.485 g, 1.79 mmol) in ethanol/water (5 ml, 4:1) and the mixture stirred for 2 h at room temperature then heated at reflux for 2 h. The reaction was poured into ice water (40 ml) and extracted with DCM (2×100 ml). The combined organic extracts were dried (MgSO$_4$), filtered and evaporated to give a brown solid. The crude product was chromatographed on silica (eluent 3% MeOH in DCM) to give the product as a pale yellow solid, which was recrystallised from DCM/isohexane (210 mg): $\delta_H$ (400 MHz, CDCl$_3$) 2.74 (3H, s), 7.40–7.47 (2H, m), 7.53–7.58 (2H, m), 8.24–8.27 (2H, m), 9.39 (1H, s); m/z (ES$^+$) 341 (M$^+$+H).

4,2'-Difluoro-5'-[3-(4-fluorophenyl)-[1,2,4]triazin-5-yl]biphenyl-2-carbonitrile To a mixture of 4,2'-difluoro-5'-(3-methylsulfanyl-[1,2,4]triazin-5-yl)biphenyl-2-carbonitrile (0.11 g, 0.32 mmol), cuprous 3-methylsalicylate (0.153 g, 0.711 mmol) and 4-fluorobenzeneboronic acid (0.1 g, 0.711 mmol) in dry THF (8 ml) was added tetrakis(triphenylphosphine)palladium(0) (0.037 g, 0.032 mmol) and the mixture heated at 50° C. for 5 h. The reaction was allowed to cool to ambient temperature, diluted with DCM (20 ml) and filtered through a glass fibre filter. The dark brown solution was evaporated to give a brown solid. The crude product was chromatographed on silica (eluted with 3% MeOH in DCM) to give the product as a yellow solid. Recrystallisation from DCM/MeOH gave the title compound as a pale yellow solid (52 mg): $\delta_H$ (400 MHz, CDCl$_3$) 7.24 (2H, m), 7.44–7.49 (2H, m), 7.55–7.62 (2H, m), 8.36–8.39 (2H, m), 8.64–8.69 (2H, m), 9.62 (1H, s); m/z (ES$^+$) 389 (M$^+$+H).

EXAMPLE 3

4,2'-Difluoro-5'-[3-(2,4-difluorophenyl)-[1,2,4]triazin-5-yl]biphenyl-2-carbonitrile 4,2'-Difluoro-5'-(3-methylsulfanyl-[1,2,4]triazin-5-yl)biphenyl-2-carbonitrile (0.15 g, 0.44 mmol) was coupled to 2,4-difluorobenzeneboronic acid (0.135 g, 0.97 mmol) by the method of Example 2 to give the title product as a pale yellow solid (124 mg): $\delta_H$ (400 MHz, CDCl$_3$) 6.99–7.11 (2H, m), 7.44–7.48 (2H, m), 7.54–7.59 (2H, m), 8.32–8.39 (3H, m) 9.65 (1H, s); m/z (ES$^+$) 407 (M$^+$+H).

EXAMPLE 4

4,2'-Difluoro-5'-[3-(2-fluorophenyl)-[1,2,4]triazin-5-yl]biphenyl-2-carbonitrile 4,2'-Difluoro-5'-(3-methylsulfanyl-[1,2,4]triazin-5-yl)biphenyl-2-carbonitrile (0.115 g, 0.338 mmol) was coupled to 2-fluorobenzeneboronic acid (0.104 g, 0.743 mmol) by the method of Example 2 to give the title product as a pale yellow solid (63 mg): $\delta_H$ (400 MHz, CDCl$_3$) 7.27 (1H, q, J 1.3 Hz), 7.32–7.37 (1H, m), 7.43–7.48 (2H, m), 7.53–7.60 (3H, m), 8.24–8.29 (1H, m), 8.35–8.39 (2H, m), 9.67 (1H, s); m/z(ES$^+$) 389 (M$^+$+H).

EXAMPLE 5

4,2'-Difluoro-5'-[3-(4-methoxyphenyl)-[1,2,4]triazin-5-yl]biphenyl-2-carbonitrile To a solution of 4-methoxyphenylhydrazide (0.576 g, 1.96 mmol) (prepared according to the procedure described in *J. Med. Chem.*, 1977, 20, 723–6) and sodium hydrogencarbonate (0.165 g, 1.967 mmol) in ethanol/water (10 ml, 4:1) was added a solution of 4,2'-difluoro-5'-(2-oxoacetyl)biphenyl-2-carbonitrile (0.485 g, 1.7882 mmol) in ethanol/water (5 ml, 4:1) and the mixture stirred for 2 h at room temperature then heated at reflux for 2 h. The reaction was cooled to ambient temperature and poured into ice water (50 ml). The precipitated solid was collected by filtration and washed with ether and dried under vacuum to give a yellow/green powdery solid. The crude product was chromatographed on silica (eluted with 3% MeOH in DCM), and the product recrystallised from ethyl acetate to give a pale yellow solid (325 mg): $\delta_H$ (400 MHz, CDCl$_3$) 3.91 (3H, s), 7.06 (2H, m), 7.43–7.49 (2H, m), 7.55–7.59 (2H, m), 8.34–8.38 (2H, m), 8.61 (2H, m), 9.55 (1H, s); m/z (ES$^+$) 401 (M$^+$+H).

EXAMPLE 6

3-(2,4-Difluorophenyl)-5-[4-fluoro-3-(3-fluoropyridin-4-yl)phenyl]-[1,2,4]triazine A mixture of 5-(3-bromo-4-fluorophenyl)-3-(2,4-difluorophenyl)-[1,2,4]triazine (from Example 8 below) (120 mg, 0.33 mmol), lithium chloride (70 mg), cuprous iodide (6.3 mg) and 3-fluoro-4-tributylstannylpyridine (120 mg, 0.31 mmol) in dry 1,4-dioxane (5 ml) was degassed under nitrogen. Tetrakis(triphenylphosphine)palladium(0) (30 mg) was added and the mixture heated under an atmosphere of nitrogen at 80° C. for 48 h. On cooling to room temperature the mixture was partitioned between dichloromethane (30 ml) and 25% aqueous ammonium hydroxide (15 ml). The organic layer was separated, solvent removed at reduced pressure, and the residue subjected to preparative thin layer chromatography on silica gel, eluent 2% methanol in dichloromethane. The product was recrystallised from hot toluene to give 3-(2,4-difluorophenyl)-5-[4-fluoro-3-(3-fluoropyridin-4-yl)phenyl]-[1,2,4]triazine as a solid (50 mg): $\delta_H$ (500 MHz, d$^6$-DMSO) 7.35 (1H, m), 7.52 (1H, m), 7.73 (2H, m), 8.34 (1H, m), 8.63 (3H, m), 8.78 (1H, s), 10.18 (1H, s); m/z (ES$^+$) 383.

EXAMPLE 7

5-[4-Fluoro-3-(3-fluoropyridin-4-yl)phenyl]-3-(4-methoxyphenyl)-[1,2,4]triazine 5-(3-Bromo-4-fluorophenyl)-3-(4-methoxyphenyl)-[1,2,4]triazine (from Example 9 below) (150 mg, 0.42 mmol) was coupled to 3-fluoro-4-tributylstannylpyridine (170 mg, 0.43 mmol) using the method of Example 6 to give 5-[4-fluoro-3-(3-fluoro-pyridin-4-yl)phenyl]-3-(4-methoxyphenyl)-[1,2,4]triazine, crystallised from hot toluene (70 mg): $\delta_H$ (400 MHz, d$^6$-DMSO) 3.88 (3H, s), 7.16 (2H, d, J 8.9 Hz), 7.69–7.77 (2H, m), 8.53 (2H, d, J 8.9 Hz), 8.63–8.67 (3H, m), 8.79 (1H, m), 10.05 (1H, s); m/z (ES$^+$) 377.

EXAMPLE 8

5-(3-Bromo-4-fluorophenyl)-3-(2.4-difluorophenyl)-[1,2,4]triazine

To 3-bromo-4-fluoroacetophenone (11.0 g) in 1,4-dioxane (160 ml) and water (15 ml) was added selenium dioxide (8.8 g). The mixture was heated at reflux for 10 h, cooled to room temperature, and the solvent then removed at reduced pressure. The residue was suspended in 50% diethyl ether in isohexane, and residual solid removed by filtration. The filtrate was dried over Na$_2$SO$_4$, and solvent then evaporated to give (3-bromo-4-fluorophenyl)oxoacetaldehyde as a yellow oil, which was used without further purification in the next step.

Crude (3-bromo-4-fluorophenyl)oxoacetaldehyde (3.83 g, 16.2 mmol) was dissolved in ethanol (25 ml) and aqueous NaHCO$_3$ (2.7 g in water (20 ml)). The mixture was cooled to −5° C., and a solution of 2,4-difluorobenzimidrazone hydrogen iodide salt (4.266 g, 13.5 mmol) in ethanol (25 ml) and water (10 ml) was added slowly with stirring. The resulting mixture was then stirred at room temperature for 16 h, and then heated at reflux for 3 h. The mixture was diluted with water (80 ml) whilst still hot, stirred briefly, then allowed to stand at room temperature for 4 h. The solid was collected by filtration, re-dissolved in hot toluene, dried over Na$_2$SO$_4$, filtered hot, and the filtrate cooled to room temperature, diluted with an equal volume of isohexane and allowed to stand. The solid was collected by filtration and dried in vacuo to give 5-(3-bromo-4-fluorophenyl)-3-(2,4-difluorophenyl)-[1,2,4]triazine (1.78 g) as an orange solid: $\delta_H$ (400 MHz, CDCl$_3$) 7.00–7.12 (2H, m), 7.34 (1H, t, J 8.3 Hz), 8.20 (1H, m), 8.33 (1H, m), 8.51 (1H, m), 9.60 (1H, s); m/z (ES$^+$) 366; 368 (M$^+$+H).

EXAMPLE 9

5-(3-Bromo-4-fluorophenyl)-3-(4-methoxyphenyl)-[1.2.4]triazine

Crude (3-bromo-4-fluorophenyl)oxoacetaldehyde was reacted with 4-methoxybenzimidrazone hydrogen iodide salt, according to the procedure of Example 8, to give 5-(3-bromo-4-fluorophenyl)-3-(4-methoxyphenyl)-[1,2,4]triazine: $\delta_H$ (400 MHz, CDCl$_3$) 3.91 (3H, s), 7.07 (2H, d, J 9.0 Hz), 7.33 (1H, t, J 8.4 Hz), 8.18 (1H, m), 8.52 (1H, m), 8.59 (1H, d, J 9.0 Hz), 9.48 (1H, s); m/z (ES$^+$) 360; 362 (M$^+$+H).

EXAMPLE 10

5-[3-(3.5-Difluoropyridin-4-yl)-4-fluorophenyl]-3-(2.4-difluorophenyl)-[1,2,4]triazine 5-(3-Bromo-4-fluorophenyl)-3-(2,4-difluorophenyl)-[1,2,4]triazine was coupled to 3,5-difluoro-4-tributylstannylpyridine using the method of Example 6 to give 5-[3-(3,5-difluoropyridin-4-yl)-4-fluorophenyl]-3-(2,4-difluorophenyl)-[1,2,4]triazine, crystallised from hot 2-propanol as a pale yellow solid: $\delta_H$ (500 MHz, d$^6$-DMSO) 7.35 (1H, m), 7.52 (1H, m), 7.79 (1H, t, J 8.9 Hz), 8.34 (1H, m), 8.71 (2H, m), 8.79 (2H, s), 10.13 (1H, s); m/z (ES$^+$) 401.

EXAMPLE 11

5-[3-(3,5-Difluoropyridin-2-yl)-4-fluorophenyl]-3-(4-methoxyphenyl)-[1,2,4]triazine 5-(3-Bromo-4-fluorophenyl)-3-(4-methoxyphenyl)-[1,2,4]triazine was coupled to 3,5-difluoro-2-trimethylstannylpyridine using the method of Example 6 to give 5-[3-(3,5-difluoropyridin-2-yl)-4-fluorophenyl]-3-(4-methoxyphenyl)-[1,2,4]triazine, crystallised from hot 2-propanol as a pale yellow solid: $\delta_H$ (500 MHz, d$^6$-DMSO) 3.88 (3H, s), 7.17 (2H, d, J 9.0 Hz), 7.69 (1H, t, J 9.1 Hz), 8.20 (1H, m), 8.52 (2H, d, J 9.0 Hz), 8.65–8.70 (2H, m), 8.77 (1H, d, J 2.2 Hz), 10.02 (1H, s); m/z (ES$^+$) 395.

EXAMPLE 12

6,2'-Difluoro-5'-[3-(2,4-difluorophenyl)-[1,2,4]triazin-5-yl]biphenyl-2-carbonitrile To a degassed mixture of 5-(3-bromo-4-fluorophenyl)-3-(2,4-difluorophenyl)-[1,2,4]triazine (0.2 g, 0.55 mmol) and 3-fluoro-2-(4,4,5,5-tetramethyl-[1,3,2]dioxaborolan-2-yl)benzonitrile (0.270 g, 1.1 mmol) in 1,4-dioxane (6 ml) and sodium carbonate (2 ml, 2N solution) was added tetrakis(triphenylphosphine)palladium(0), and the mixture heated at 80° C. Fog 24 h. The mixture was cooled to ambient temperature and partitioned between water (30 ml) and dichloromethane (40 ml). The aqueous layer was extracted with dichloromethane (2×40 ml) and the combined organics dried over Mg$_2$SO$_4$, filtered and the solvent removed at reduced pressure. The crude product was chromatographed on silica gel, eluent 5% ethyl acetate in dichloromethane, to give the product as a pale yellow solid (0.014 g): $\delta_H$ (400 MHz, CDCl$_3$) 6.99–7.10 (2H, m), 7.49 (4H, m), 8.30–8.44 (3H, m), 9.69 (1H, dd, J 0.8, 2.0 Hz); m/z (ES$^+$) 407.

EXAMPLE 13

3-(2,4-Difluorophenyl)-5-(2-fluoro-2'-trifluoromethylbiphenyl-5-yl)-[1,2,4]triazine 5-(3-Bromo-4-fluorophenyl)-3-(2,4-difluorophenyl)-[1,2,4]triazine was coupled to 2-trifluoromethylphenylboronic acid by the method of Example 12 to give 3-(2,4-difluorophenyl)-5-(2-fluoro-2'-trifluoromethylbiphenyl-5-yl)-[1,2,4]triazine as a pale yellow solid: $\delta_H$ (400 MHz, CDCl$_3$) 6.98–7.09 (2H, m), 7.35–7.42 (2H, m), 7.65 (2H, dd, J 7.4, 17.6 Hz), 7.84 (1H, d, J 7.8 Hz), 8.21 (1H, dd, J 2.2, 6.8 Hz), 8.28–8.36 (2H, m), 9.61 (1H, s); m/z (ES$^+$) 432.

EXAMPLE 14

5-(2,2'-Difluorobiphenyl-5-yl)-3-(2,4-difluorophenyl)-[1,2,4]triazine 5-(3-Bromo-4-fluorophenyl)-3-(2,4-difluorophenyl)-[1,2,4]triazine was coupled to 2-fluorophenylboronic acid by the method of Example 12 to give 5-(2,2'-difluorobiphenyl-5-yl)-3-(2,4-difluorophenyl)-[1,2,4]triazine as a fluffy yellow solid: $\delta_H$ (400 MHz, CDCl$_3$) 6.99–7.10 (2H, m), 7.21–7.23 (1H, m), 7.27–7.31 (1H, m), 7.37–7.48 (3H, m), 8.29–8.35 (3H, m), 9.64 (1H, s); m/z (ES$^+$) 382.

EXAMPLE 15

5,2'-Difluoro-5'-[3-(2,4-difluorophenyl)-[1,2,4]triazin-5-yl]biphenyl-2-carbonitrile 5-(3-Bromo-4-fluorophenyl)-3-(2,4-difluorophenyl)-[1,2,4]triazine was coupled to 4-fluoro-2-(4,4,5,5-tetramethyl-[1,3,2]dioxaborolan-2-yl)-benzonitrile by the method of Example 12 to give 5,2'-difluoro-5'-[3-(2,4-difluorophenyl)-[1,2,4]triazin-5-yl]biphenyl-2-carbonitrile as a yellow solid: $\delta_H$ (400 MHz, CDCl$_3$) 6.99–7.11 (2H, m), 7.27–7.34 (2H, m), 7.47 (1H, t, J 9.4 Hz), 7.87 (1H, dd, J 5.5, 8.6 Hz), 8.30–8.41 (3H, m), 9.66 (1H, s); m/z (ES$^+$) 407.

Also isolated from the above reaction was the corresponding amide 5,2'-difluoro-5'-[3-(2,4-difluorophenyl)-[1,2,4]triazin-5-yl]biphenyl-2-carboxamide as a tan coloured solid; m/z (ES$^+$) 425.

EXAMPLE 16

3,2'-Difluoro-5'-[3-(2,4-difluorophenyl)-[1,2,4]triazin-5-yl]biphenyl-2-carbonitrile 5-(3-Bromo-4-fluorophenyl)-3-(2,4-difluorophenyl)-[1,2,4]triazine was coupled to 6-fluoro-2-(4,4,5,5-tetramethyl-[1,3,2]dioxaborolan-2-yl)-benzonitrile by the method of Example 12 to give 3,2'-difluoro-5'-[3-(2,4-difluorophenyl)-[1,2,4]triazin-5-yl]biphenyl-2-carbonitrile as a yellow solid: $\delta_H$ (400 MHz, CDCl$_3$) 6.99–7.11 (2H, m), 7.32–7.40 (2H, m), 7.47 (1H, t, J 9.2 Hz), 7.70–7.76 (1H, m), 8.30–8.40 (3H, m), 9.66 (1H, s); m/z(ES$^+$) 407.

EXAMPLE 17

5-[3-(2,4-Difluorophenyl)-[1,2,4]triazin-5-yl]-2-fluorobenzonitrile

A mixture of 5-(3-bromo-4-fluorophenyl)-3-(2,4-difluorophenyl)-[1,2,4]triazine (0.1 g, 0.27 mmol), zinc cyanide (0.032 g, 0.27 mmol) and tetrakis(triphenylphosphine)palladium(0) (0.016 g, 0.01 mmol) in N,N-dimethylformamide (4 ml) was heated to 150° C. Fog 600 s in a Smith Synthesiser microwave reactor (Personal Chemistry, Uppsala, Sweden). The reaction was partitioned between ethyl acetate (80 ml) and water (40 ml). The organic layer was washed with water (40 ml) and the combined organics dried over $Mg_2SO_4$, filtered and the solvent removed at reduced pressure. The crude product was chromatographed on silica gel, eluent 50% ethyl acetate in isohexane, to give 5-[3-(2,4-difluorophenyl)-[1,2,4]triazin-5-yl]-2-fluorobenzonitrile as a yellow solid (0.054 g): $\delta_H$ (400 MHz, $CDCl_3$) 7.02–7.14 (2H, m), 7.48 (1H, t, J 8.6 Hz), 8.33–8.39 (1H, m), 8.49–8.53 (1H, m), 8.62 (1H, dd, J 2.2, 6.1 Hz), 9.65 (1H, s); m/z($ES^+$) 313.

EXAMPLE 18

3-(2-Fluorophenyl)-5-[4-fluoro-3-(pyridin-3-yl) phenyl]-[1,2,4]triazine 5-(3-Bromo-4-fluorophenyl)-3-methylsulfanyl-[1,2,4] triazine (3-Bromo-4-fluorophenyl)oxoacetaldehyde (from Example 8) was reacted with methylthiosemicarbazide hydrogen iodide (by the method in Example 2) to give 5-(3-bromo-4-fluorophenyl)-3-methylsulfanyl-[1,2,4] triazine as a yellow solid: $\delta_H$ (400 MHz, $CDCl_3$) 2.74 (3H, s), 7.30 (1H, t, J 8.2 Hz), 8.09 (1H, m), 8.42 (1H, dd, J 2.2, 6.5 Hz), 9.33 (1H, s); m/z ($ES^+$) 300:302 (1:1).

5-[4-Fluoro-3-(pyridin-3-yl)phenyl]-3-methylsulfanyl-[1,2,4]triazine 5-(3-Bromo-4-fluorophenyl)-3-methylsulfanyl-[1,2,4] triazine was coupled to diethyl(3-pyridyl)borane by the method of Example 12 to give 5-[4-fluoro-3-(pyridin-3-yl) phenyl]-3-methylsulfanyl-[1,2,4]triazine as a yellow solid: $\delta_H$ (400 MHz, $CDCl_3$) 2.74 (3H, s), 7.37–7.46 (2H, m), 7.91–7.95 (1H, m), 8.16–8.20 (1H, m), 8.30 (1H, dd, J 2.3, 7.4 Hz), 8.70 (1H, dd, J 1.4, 4.9 Hz), 8.86 (1H, s), 9.40 (1H, s); m/z ($ES^+$) 299.

3-(2-Fluorophenyl)-5-[4-fluoro-3-(pyridin-3-yl)phenyl]-[1, 2,4]triazine

5-[4-Fluoro-3-(pyridin-3-yl)phenyl]-3-methylsulfanyl-[1, 2,4]triazine was coupled to 2-fluorophenylboronic acid by the method of Example 2 to give 3-(2-fluorophenyl)-5-[4-fluoro-3-(pyridin-3-yl)phenyl]-[1,2,4]triazine as a yellow solid: $\delta_H$ (400 MHz, $CDCl_3$) 7.28–7.30 (1H, m), 7.33–7.47 (3H, m), 7.52–7.59 (1H, m), 7.97 (1H, dd, J 2.0, 8.2 Hz), 8.25–8.32 (2H, m), 8.44 (1H, dd, J 2.3, 7.4 Hz), 8.70 (1H, d, J 2.7 Hz), 8.89 (1H, s), 9.67 (1H, s); m/z ($ES^+$) 347.

EXAMPLE 19

5-[4-Fluoro-3-(pyridin-3-yl)phenyl]-3-(4-methoxyphenyl)-[1,2,4]triazine

5-[4-Fluoro-3-(pyridin-3-yl)phenyl]-3-methylsulfanyl-[1, 2,4]triazine was coupled to 4-methoxyphenylboronic acid by the method of Example 2 to give 5-[4-fluoro-3-(pyridin-3-yl)phenyl]-3-(4-methoxyphenyl)-[1,2,4]triazine as an orange solid: $\delta_H$ (400 MHz, $CDCl_3$) 7.18 (2H, dd, J 7.2, 7.2 Hz), 7.76 (1H, m), 8.27 (1H, m), 8.57 (2H, m), 8.71 (1H, m), 8.83 (1H, m), 8.98 (1H, m), 9.10 (1H, m), 9.48 (1H, m), 10.10 (1H, s); m/z ($ES^+$) 359.

EXAMPLE 20

3-(2,4-Difluorophenyl)-5-[4-fluoro-3-(pyridin-3-yl) phenyl]-[1,2,4]triazine

5-[4-Fluoro-3-(pyridin-3-yl)phenyl]-3-methylsulfanyl-[1, 2,4]triazine was coupled to 2,4-difluorophenylboronic acid by the method of Example 2 to give 3-(2,4-difluorophenyl)-5-[4-fluoro-3-(pyridin-3-yl)phenyl]-[1,2,4]triazine as a yellow solid: $\delta_H$ (400 MHz, $CDCl_3$) 7.00–7.12 (2H, m), 7.42 (2H, m), 7.96 (1H, dd, J 2.0, 7.8 Hz), 8.27–8.36 (2H, m), 8.42 (1H, dd, J 2.5, 7.2 Hz), 8.70 (1H, s), 8.89 (1H, s), 9.66 (1H, s); m/z ($ES^+$) 365.

EXAMPLE 21

5-[4-Fluoro-3-(pyridin-2-yl)phenyl]-3-(pyridin-2-yl)-[1,2,4]triazine

To a mixture of 5-(3-bromo-4-fluorophenyl)-3-methylsulfanyl-[1,2,4]triazine (0.2 g, 0.67 mmol), cuprous 3-methylsalicylate (0.315 g, 1.5 mmol), 2-(tri-n-butylstannyl)pyridine (0.736 g, 2.2 mmol) and lithium chloride (0.085 g, 2.0 mmol) in dry 1,4-dioxane (8 ml) was added tetrakis(triphenylphosphine)palladium(0) (0.077 g, 0.032 mmol) and the mixture heated at 60° C. Fog 24 h. The reaction was allowed to cool to ambient temperature, diluted with DCM (20 ml) and washed with 10% ammonia solution (10 ml). The organic layer was washed with water (40 ml) and the combined organics dried over $Mg_2SO_4$, filtered and the solvent removed at reduced pressure. The crude product was purified by preparative thin-layer chromatography on silica gel, eluent 3% methanol in dichloromethane. The solid obtained was triturated with diethyl ether to give 5-[4-fluoro-3-(pyridin-2-yl)phenyl]-3-(pyridin-2-yl)-[1,2,4] triazine as a powdery orange solid (35 mg): $\delta_H$ (400 MHz, $CDCl_3$) 7.39–7.48 (3H, m), 7.51 (1H, m), 7.81–8.00 (3H, m), 8.47 (1H, m), 8.71 (1H, m), 8.80 (1H, m), 8.93 (1H, m), 9.81 (1H, s); m/z ($ES^+$) 330 ($M^+$+H).

EXAMPLE 22

2-{5-[3-(2,4-Difluorophenyl)-[1,2,4]triazin-5-yl]-2-fluorophenyl}propan-2-ol

A solution of 5-(3-bromo-4-fluorophenyl)-3-(2,4-difluorophenyl)-[1,2,4]triazine (200 mg, 0.55 mmol) was formed in 1,4-dioxane (4 ml). Tributyl(1-ethoxyvinyl)tin (0.2 ml, 0.60 mmol) and tetrakis(triphenylphosphine) palladium(0) (50 mg) were added and the mixture was heated to 150° C. Fog 700 s in a Smith Synthesiser microwave reactor (Personal Chemistry, Uppsala, Sweden). The mixture was poured into aqueous hydrochloric acid (2M, 20 ml) and stirred at room temperature for 30 min. Ethyl acetate (20 ml) was added and the mixture was stirred for a further 3 h. The mixture was extracted with ethyl acetate (2×20 ml) and the combined organics were dried over anhydrous magnesium sulphate, filtered and evaporated to an orange solid. Purification by flash column chromatography over silica using 90% dichloromethane: 10% ethyl acetate as eluent, then recrystallisation from dichloromethane using isohexane, gave 1-{5-[3-(2,4-difluorophenyl)-[1,2,4]triazin-5-yl]-2-fluorophenyl}ethanone as a yellow solid: m/z ($ES^+$) 330.

A solution of 1-{5-[3-(2,4-difluorophenyl)-[1,2,4]triazin-5-yl]-2-fluoro-phenyl}ethanone (100 mg, 0.30 mmol) was formed in tetrahydrofuran (20 ml) and cooled to −78° C. Methylmagnesium chloride (3M in tetrahydrofuran, 0.11 ml, 0.33 mmol) was added and the mixture stirred at −78° C. Fog 20 min. The reaction was quenched with saturated aqueous ammonium chloride (10 ml) and the mixture allowed to warm to room temperature then poured into water (20 ml) and extracted with ethyl acetate (2×20 ml). The combined organics were dried over anhydrous magnesium sulphate, filtered and evaporated to give a yellow solid. Purification by flash column chromatography over silica using 60% dichloromethane: 40% ethyl acetate as eluent, then recrystallisation from dichloromethane using isohexane, gave 2-{5-[3-(2,4-difluorophenyl)-[1,2,4]triazin-5-yl]-2-fluorophenyl}propan-2-ol as a yellow solid (50 mg): $\delta_H$ (400 MHz, CDCl$_3$) 1.72 (6H, s), 2.12 (1H, d, J 2 Hz), 6.99–7.10 (2H, m), 7.24 (1H, dd, J 8 and 11 Hz), 8.18–8.22 (1H, m), 8.29–8.35 (1H, m), 8.57 (1H, dd, J 2 and 8 Hz), 9.64 (1H, s); m/z (ES$^+$) 346.

EXAMPLE 23

3-(2.4-Difluorophenyl)-5-[4-fluoro-3-(1-methoxy-1-methylethyl)phenyl]-[1,2,4]triazine A solution of 2-{5-[3-(2,4-difluorophenyl)-[1,2,4]triazin-5-yl]-2-fluorophenyl}propan-2-ol (40 mg, 0.11 mmol) was formed in N,N-dimethylformamide (5 ml) and cooled to 0° C. Sodium hydride (60% in mineral oil, 5 mg, 0.13 mmol) was added and the mixture was stirred at 0° C. Fog 20 min. Methyl iodide (0.01 ml, 0.23 mmol) was added and the mixture stirred for a further 1.5 h at 0° C. Water (5 ml) was added and the mixture poured into water (20 ml) then extracted with ethyl acetate (2×20 ml). The combined organics were dried over anhydrous magnesium sulphate, filtered and evaporated to give a yellow oil. Purification by preparative thin layer chromatography using 97% dichloromethane:3% ethyl acetate as eluent gave 3-(2,4-difluorophenyl)-5-[4-fluoro-3-(1-methoxy-1-methylethyl)phenyl]-[1,2,4]triazine as a yellow solid (15 mg): $\delta_H$ (400 MHz, CDCl$_3$) 1.66 (6H, d, J 1 Hz), 3.30 (3H, s), 6.99–7.11 (2H, m), 7.25 (1H, dd, J 3 and 7 Hz), 8.17–8.22 (1H, m), 8.31–8.37 (1H, m), 8.41 (1H, dd, J 2 and 8 Hz), 9.63 (1H, s); m/z (ES$^+$) 360.

EXAMPLE 24

5-(4-Fluoro-3-trifluoromethylphenyl)-3-(4-methoxyphenyl)-[1,2,4]triazine

A solution of 4-methoxythiobenzamide (11 g, 65.8 mmol) was formed in acetone (50 ml). Methyl iodide (5.6 ml, 89.7 mmol) was added and the mixture heated to reflux, then maintained at 60° C. Fog 2.5 h and allowed to cool to ambient temperature. Diethyl ether (50 ml) was added and the precipitate was filtered, washed with diethyl ether (100 ml), and dried under vacuum to give 4-methoxythiobenzimidic acid methyl ester hydriodide salt as a cream solid (19.6 g): m/z (ES$^+$) 182.

A solution of hydrazine monohydrate (3.7 ml, 76.2 mmol) was formed in methanol (120 ml) and cooled to –10° C. A solution of 4-methoxythiobenzimidic acid methyl ester hydriodide salt (19.6 g, 63.5 mmol) in tetrahydrofuran (120 ml) and methanol (80 ml) was added to the cooled solution via cannula over 20 min. The mixture was stirred at –5° C. Fog 2 h then allowed to warm to room temperature for 1 h. Tetrahydrofuran (200 ml) was added then the mixture concentrated on a rotary evaporator to ~150 ml. A 1:1 mixture of diethyl ether:tetrahydrofuran (400 ml) was added and the resulting precipitate was filtered and washed with further 1:1 diethyl ether:tetrahydrofuran (100 ml) then dried under vacuum to give 4-methoxybenzenecarboximidic hydrazide hydriodide salt as a white solid (15.6 g): m/z (ES$^+$) 166.

4-Fluoro-3-(trifluoromethyl)acetophenone (2 g, 9.70 mmol) was reacted with selenium dioxide (1.6 g, 14.6 mmol) using the method described in Example 1 to give crude (4-fluoro-3-trifluoromethylphenyl)-oxoacetaldehyde as a yellow oil: m/z (ES$^+$) 221.

(4-Fluoro-3-trifluoromethylphenyl)oxoacetaldehyde was reacted with 4-methoxybenzenecarboximidic hydrazide hydriodide salt (2.37 g, 8.08 mmol) using the method described in Example 1 to give 5-(4-fluoro-3-trifluoromethylphenyl)-3-(4-methoxyphenyl)-[1,2,4]triazine as a yellow solid (1.13 g): $\delta_H$ (400 MHz, CDCl$_3$) 3.92 (3H, s), 7.06–7.10 (2H, m), 7.44 (1H, t, J 9.2 Hz), 8.44–8.49 (1H, m), 8.56 (1H, dd, J 2.0, 6.7 Hz), 8.58–8.62 (2H, m), 9.54 (1H, s); m/z (ES$^+$) 350.

EXAMPLE 25

3-(4-Methoxyphenyl)-5-(3-trifluoromethoxyphenyl)-[1,2,4]triazine 3-(Trifluoromethoxy)acetophenone (2 g, 9.80 mmol) was reacted with selenium dioxide (1.63 g, 14.7 mmol) using the method described in Example 1 to give crude (3-trifluoromethoxyphenyl)oxoacetaldehyde as a yellow oil: m/z (ES$^+$) 219.

(3-Trifluoromethoxyphenyl)oxoacetaldehyde was reacted with 4-methoxybenzenecarboximidic hydrazide hydriodide salt (2.39 g, 8.16 mmol) using the method described in Example 1 to give 3-(4-methoxyphenyl)-5-(3-trifluoromethoxyphenyl)-[1,2,4]triazine as a yellow solid (1.10 g): $\delta_H$ (400 MHz, CDCl$_3$) 3.92 (3H, s), 7.06–7.10 (2H, m), 7.45–7.49 (1H, m), 7.64 (1H, t, J 8.2 Hz), 8.14–8.18 (2H, m), 8.59–8.63 (2H, m), 9.53 (1H, s); m/z (ES$^+$) 348.

EXAMPLE 26

3-(2,4-Difluorophenyl)-5-(4-fluoro-3-trifluoromethylphenyl)-[1,2,4]triazine 2,4-Difluorobenzenecarboximidic hydrazide hydriodide salt was made from 2,4-difluorothiobenzamide using the method described in Example 24. (4-Fluoro-3-trifluoromethylphenyl)oxoacetaldehyde was reacted with 2,4-difluorobenzenecarboximidic hydrazide hydriodide salt using the method described in Example 1 to give 3-(2,4-difluorophenyl)-5-(4-fluoro-3-trifluoromethylphenyl)-[1,2,4]triazine as a yellow solid (795 mg): $\delta_H$ (400 MHz, CDCl$_3$) 7.01–7.13 (2H, m), 7.45 (1H, t, J 9.2 Hz), 8.32–8.38 (1H, m), 8.46–8.50 (1H, m), 8.55 (1H, dd, J 2.3, 6.7 Hz), 9.66 (1H, s); m/z (ES$^+$) 356.

EXAMPLE 27

3-(2,4-Difluorophenyl)-5-(3-trifluoromethoxyphenyl)-[1,2,4]triazine (3-Trifluoromethoxyphenyl)oxoacetaldehyde was reacted with 2,4-difluorobenzenecarboximidic hydrazide hydriodide salt using the method described in Example 1 to give 3-(2,4-difluorophenyl)-5-(3-trifluoromethoxyphenyl)-[1,2,4]triazine as a yellow solid (655 mg): $\delta_H$ (400 MHz, CDCl$_3$) 7.01–7.12 (2H, m), 7.47–7.51 (1H, m), 7.65 (1H, t, J 8.2 Hz), 8.15–8.18 (2H, m), 8.32–8.38 (1H, m), 9.64 (1H, s); m/z (ES$^+$) 354.

EXAMPLE 28

3-(2,4-Difluorophenyl)-5-(3-trifluoromethylsulfanylphenyl)-[1,2,4]triazine

3-Trifluoromethylsulfanylacetophenone (2 g, 9.08 mmol) was reacted with selenium dioxide (1.51 g, 13.6 mmol) using the method described in Example 1 to give crude (3-trifluoromethylsulfanylphenyl)-oxoacetaldehyde as a yellow oil: m/z (ES$^+$) 235.

(3-Trifluoromethylsulfanylphenyl)oxoacetaldehyde was reacted with 2,4-difluorobenzenecarboximidic hydrazide hydriodide salt (1.13 g, 3.78 mmol) using the method described in Example 1 to give 3-(2,4-difluorophenyl)-5-(3-trifluoromethylsulfanylphenyl)-[1,2,4]triazine as a yellow solid (1.0 g): $\delta_H$ (400 MHz, CDCl$_3$) 7.01–7.13 (2H, m), 7.68 (1H, t, J 7.8 Hz), 7.92 (1H, d, J 7.4 Hz), 8.32–8.39 (2H, m), 8.55 (1H, s), 9.67 (1H, s); m/z (ES$^+$) 370.

EXAMPLE 29

3-(4-Methoxyphenyl)-5-(3-trifluoromethylsulfanylphenyl)-[1,2,4]triazine (3-Trifluoromethylsulfanylphenyl)oxoacetaldehyde was reacted with 4-methoxybenzenecarboximidic hydrazide hydriodide salt (1.11 g, 3.78 mmol) using the method described in Example 1 to give 3-(4-methoxyphenyl)-5-(3-trifluoromethylsulfanylphenyl)-[1,2,4]triazine as a yellow solid (820 g): $\delta_H$ (400 MHz, CDCl$_3$) 3.92 (3H, s), 7.06–7.10 (2H, m), 7.67 (1H, t, J 7.8 Hz), 7.90 (1H, d, J 7.8 Hz), 8.35–8.39 (1H, m), 8.56 (1H, s), 8.60–8.64 (2H, m), 9.55 (1H, s); m/z (ES$^+$) 364.

EXAMPLE 30

1-{3-[3-(2 4-Difluorophenyl)-[1,2,4]triazin-5-yl]phenyl}pyrrolidin-2-one

A solution of 3-aminoacetophenone (10 g, 74 mmol) and N,N-diisopropylethylamine (14.2 ml, 81 mmol) was formed in tetrahydrofuran (200 ml) and cooled to 0° C. A solution of 4-chlorobutyryl chloride (8.3 ml, 74 mmol) in tetrahydrofuran (75 ml) was added dropwise to this solution and the mixture was left to stir at 0° C. Fog 2 h. The mixture was concentrated on the rotary evaporator and the residue was diluted with ethyl acetate (300 ml) and washed with saturated aqueous ammonium chloride (2×200 ml), then dried over anhydrous magnesium sulphate, filtered and concentrated. Isohexane was added to crystallise N-(3-acetylphenyl)-4-chlorobutyramide as a white solid (15.5 g): m/z (ES$^+$) 240.

A solution of N-(3-acetylphenyl)-4-chlorobutyramide (3 g, 12.5 mmol) was formed in N,N-dimethylformamide (100 ml) and cooled to 0° C. Sodium hydride (60% in mineral oil, 550 mg, 13.8 mmol) was added in portions and the mixture was stirred at 0° C. Fog 2 h. The reaction was quenched with water (10 ml) then poured into water (400 ml) and extracted with ethyl acetate (3×200 ml). The combined organics were dried over anhydrous magnesium sulphate, filtered and evaporated to give a yellow oil. Purification by flash column chromatography over silica using ethyl acetate as eluent gave 1-(3-acetylphenyl)pyrrolidin-2-one as a white solid: m/z (ES$^+$) 204.

1-(3-Acetylphenyl)pyrrolidin-2-one (1.2 g, 5.9 mmol) was reacted with selenium dioxide (0.98 g, 8.9 mmol) using the method described in Example 1 to give crude oxo[3-(2-oxopyrrolidin-1-yl)phenyl]acetaldehyde as a yellow oil: m/z (ES$^+$) 218.

Oxo[3-(2-oxopyrrolidin-1-yl)phenyl]acetaldehyde was reacted with 2,4-difluorobenzenecarboximidic hydrazide hydriodide salt (0.74 g, 2.46 mmol) using the method described in Example 1 to give 1-{3-[3-(2,4-difluorophenyl)-[1,2,4]triazin-5-yl]phenyl}pyrrolidin-2-one as a yellow solid (0.5 g): $\delta_H$ H (400 MHz, d$^6$-DMSO) 2.08–2.16 (2H, m), 2.55 (2H, t, J 8.2 Hz), 3.96 (2H, t, J 7.0 Hz), 7.34–7.39 (1H, m), 7.49–7.56 (1H, m), 7.65 (1H, t, J 8.0 Hz), 8.00–8.03 (1H, m), 8.16 (1H, d, J 7.8 Hz), 8.27–8.33 (1H, m), 8.59 (1H, t, J 1.8 Hz), 10.08 (1H, s); m/z (ES$^+$) 353.

EXAMPLE 31

1-{3-[3-(4-Methoxyphenyl)-[1,24]triazin-5-yl]phenyl}pyrrolidin-2-one

Oxo[3-(2-oxopyrrolidin-1-yl)phenyl]acetaldehyde was reacted with 4-methoxybenzenecarboximidic hydrazide hydriodide salt (0.72 g, 2.46 mmol) using the method described in Example 1 to give 1-{3-[3-(4-methoxyphenyl)-[1,2,4]triazin-5-yl]phenyl}pyrrolidin-2-one as a yellow solid (0.47 g): $\delta_H$ (400 MHz, d$^6$-DMSO) 2.09–2.17 (2H, m), 2.57 (2H, t, J 8.0 Hz), 3.88 (3H, s), 3.99 (2H, t, J 7.0 Hz), 7.16–7.21 (2H, m), 7.64 (1H, t, J 8.0 Hz), 7.98–8.01 (1H, m), 8.18 (1H, d, J 8.2 Hz), 8.51–8.55 (2H, m), 8.66 (1H, t, J 1.8 Hz), 9.95 (1H, s); m/z (ES$^+$) 347.

EXAMPLE 32

3-(2,4-Difluorophenyl)-5-(3-trifluoromethanesulfinylphenyl)-[1,2,4]triazine 1-oxide A solution of 3-(2,4-difluorophenyl)-5-(3-trifluoromethylsulfanyl-phenyl)-[1,2,4]triazine (100 mg, 0.27 mmol) was formed in dichloromethane (4 ml). A solution of m-chloroperoxybenzoic acid (55%, 161 mg, 0.51 mmol) in dichloromethane (1 ml) was added and the mixture was stirred at room temperature for 2 days. The mixture was poured into aqueous sodium carbonate (2M, 10 ml) and extracted with dichloromethane (10 ml). The organic phase was dried over anhydrous magnesium sulphate, filtered and evaporated to give a yellow solid. Purification by flash column chromatography over silica, using dichloromethane containing 20% ethyl acetate as eluent, gave 3-(2,4-difluorophenyl)-5-(3-trifluoromethanesulfinylphenyl)-[1,2,4]triazine 1-oxide as a yellow solid (40 mg): $\delta_H$ (400 MHz, d$^6$-DMSO) 7.33–7.39 (1H, m), 7.49–7.56 (1H, m), 7.97 (1H, t, J 7.8 Hz), 8.16–8.27 (2H, m), 8.64–8.67 (1H, m), 8.80 (1H, s), 9.33 (1H, s); m/z (ES$^+$) 402.

EXAMPLE 33

5'-[3-(2,4-Difluorophenyl)-[1,2,4]triazin-5-yl]-2'-fluorobiphenyl-4-carbonitrile A solution of 5-(3-bromo-4-fluorophenyl)-3-(2,4-difluorophenyl)-[1,2,4]triazine (100 mg, 0.27 mmol) and 4-cyanophenylboronic acid (48 mg, 0.33 mmol) was formed in 1,4-dioxane (4 ml) with aqueous sodium carbonate (2M, 1 ml). Tetrakis(triphenylphosphine)palladium(0) (20 mg) was added and the mixture was heated to 150° C. Fog 700 s in a Smith Synthesiser microwave reactor. The solvent was removed and the residue purified by flash column chromatography over silica using dichloromethane as eluent. Recrystallisation from dichloromethane using isohexane gave 5'-[3-(2,4-difluorophenyl)-[1,2,4]triazin-5-yl]-2'-fluorobiphenyl-4-carbonitrile as a tan solid (45 mg): $\delta_H$ (400 MHz, CDCl$_3$) 7.00–7.12 (2H, m), 7.43 (1H, t, J9.4 Hz), 7.74 (2H, d, J 8.6 Hz), 7.82 (2H, d, J 8.2 Hz), 8.27–8.41 (3H, m), 9.66 (1H, d, J 0.8 Hz); m/z (ES$^+$) 389.

EXAMPLE 34

3-(2,4-Difluorophenyl)-5-[4-fluoro-3-(3-fluoropyridin-2-yl)phenyl]-[1,2,4]triazine 5 5-(3-Bromo-4-fluorophenyl)-3-(2,4-difluorophenyl)-[1,2,4]triazine (100 mg, 0.27 mmol) was coupled to 3-fluoro-2-tributylstannylpyridine (127 mg, 0.33 mmol) using the method described in Example 22 to give 3-(2,4-difluorophenyl)-5-[4-fluoro-3-(3-fluoropyridin-2-yl)phenyl]-[1,2,4]triazine as a pale yellow solid (60 mg): $\delta_H$ (400 MHz, CDCl$_3$) 6.99–7.10 (2H, m), 7.39–7.47 (2H, m), 7.56–7.61 (1H, m), 8.29–8.36 (1H, m), 8.41–8.45 (1H, m), 8.53 (1H, dd, J 2.3, 6.7 Hz), 8.60–8.63 (1H, m), 9.68 (1H, s); m/z (ES$^+$) 383.

EXAMPLE 35

5-[4-Fluoro-3-(3-fluoropyridin-2-yl)phenyl]-3-(4-methoxyphenyl)-[1,2,4]triazine 5-(3-Bromo-4-fluorophenyl)-3-(4-methoxyphenyl)-[1,2,4]triazine (100 mg, 0.28 mmol) was coupled to 3-fluoro-2-tributylstannylpyridine (129 mg, 0.33 mmol) using the method described in Example 22 to give 5-[4-fluoro-3-(3-fluoropyridin-2-yl)phenyl]-3-(4-methoxyphenyl)-[1,2,4]triazine as a pale yellow solid (40 mg): $\delta_H$ (400 MHz, CDCl$_3$) 3.91 (3H, s), 7.04–7.08 (2H, m), 7.39–7.47 (2H, m), 7.56–7.61 (1H, m), 8.41–8.45 (1H, m), 8.54 (1H, dd, J 2.3, 6.7 Hz), 8.60–8.64 (3H, m), 9.57 (1H, s); m/z (ES$^+$) 377.

EXAMPLE 36

5-[4-Fluoro-3-(3-fluoropyridin-2-yl)phenyl]-3-(3-fluoropyridin-4-yl)-[1,2,4]triazine A solution of 5-(3-bromo-4-fluorophenyl)-3-methylsulfanyl-[1,2,4]triazine (200 mg, 0.67 mmol) and 3-fluoro-2-tributylstannylpyridine (270 mg, 0.70 mmol) was formed in 1,4-dioxane (3 ml). Tetrakis(triphenylphosphine)palladium(0) (30 mg) and copper(I) iodide (6 mg, 0.03 mmol) were added and the mixture was heated to 150° C. Fog 700 s in a Smith Synthesiser microwave reactor. The solvent was removed and the residue purified by flash column chromatography over silica using a 1:1 mixture of dichloromethane and ethyl acetate as eluent. Recrystallisation from toluene using isohexane gave 5-[4-fluoro-3-(3-fluoropyridin-2-yl)phenyl]-3-methylsulfanyl-[1,2,4]triazine as a brown solid (100 mg): $\delta_H$ (400 MHz, CDCl$_3$) 2.73 (3H, s), 7.35–7.46 (2H, m), 7.55–7.60 (1H, m), 8.29–8.33 (1H, m), 8.44 (1H, dd, J 2.3, 6.7 Hz), 8.59–8.62 (1H, m), 9.41 (1H, s); m/z (ES$^+$) 317.

A solution of 5-[4-fluoro-3-(3-fluoropyridin-2-yl)phenyl]-3-methylsulfanyl-[1,2,4]triazine (70 mg, 0.22 mmol) and 3-fluoro-4-tributylstannylpyridine (103 mg, 0.27 mmol) was formed in 1,4-dioxane (3 ml). Tetrakis(triphenylphosphine)palladium(0) (30 mg), lithium chloride (28 mg, 0.66 mmol) and copper(I) 2-hydroxy-3-methylbenzoate (104 mg, 0.49 mmol) was added and the mixture was heated to 150° C. Fog 700 s in a Smith Synthesiser microwave reactor. The solvent was removed and the residue purified by flash column chromatography over silica using a graduated eluent from a 1:1 mixture of dichloromethane and ethyl acetate to 100% ethyl acetate. The resulting tan solid was dissolved in dichloromethane (20 ml) and washed with aqueous ammonia (10%, 10 ml), then dried over anhydrous magnesium sulphate, filtered and evaporated. The resulting solid was triturated with diethyl ether to give 5-[4-fluoro-3(3-fluoropyridin-2-yl)phenyl]-3-(3-fluoropyridin-4-yl)-[1,2,4]triazine as a yellow solid (27 mg): $\delta_H$ (400 MHz, CDCl$_3$) 7.42–7.47 (2H, m), 7.57–7.61 (1H, m), 8.20 (1H, dd, J 5.1, 6.4 Hz), 8.43–8.47 (1H, m), 8.56 (1H, dd, J 2.3, 6.5 Hz), 8.61–8.65 (2H, m), 8.72 (1H, d, J 2.7 Hz), 9.77 (1H, s); m/z (ES$^+$) 366.

EXAMPLE 37

3-(2,4-Difluorophenyl)-5-(4-fluoro-3-trifluoromethylphenyl)-[1,2,4]triazine 1-oxide 3-(2,4-Difluorophenyl)-5-(4-fluoro-3-trifluoromethylphenyl)-[1,2,4]triazine (100 mg, 0.28 mmol) was oxidised using the method described in Example 32 to give 3-(2,4-difluorophenyl)-5-(4-fluoro-3-trifluoromethylphenyl)-[1,2,4]triazine 1-oxide as a yellow solid (75 mg): $\delta_H$ (400 MHz, CDCl$_3$) 6.98–7.09 (2H, m), 7.44 (1H, t, J 9.2 Hz), 8.20–8.27 (1H, m), 8.30–8.34 (1H, m), 8.40–8.44 (2H, m); m/z (ES$^+$) 372.

EXAMPLE 38

5-[4-Fluoro-3-(3-fluoropyridin-2-yl)phenyl]-3-(3-fluoropyridin-2-yl)-[1,2,4]triazine 5-[4-Fluoro-3-(3-fluoropyridin-2-yl)phenyl]-3-methylsulfanyl-[1,2,4]triazine (100 mg, 0.32 mmol) was coupled to 3-fluoro-2-tributylstannylpyridine (146 mg, 0.38 mmol) using the method described in Example 36 to give 5-[4-fluoro-3-(3-fluoropyridin-2-yl)phenyl]-3-(3-fluoropyridin-2-yl)-[1,2,4]triazine as a yellow solid (14 mg): $\delta_H$ (400 MHz, CDCl$_3$) 7.38–7.46 (2H, m), 7.52–7.60 (2H, m), 7.64–7.70 (1H, m), 8.44–8.48 (1H, m), 8.54 (1H, dd, J 2.3, 6.7 Hz), 8.59–8.61 (1H, m), 8.71 (1H, d, J 4.3 Hz), 9.79 (1H, s); m/z (ES$^+$) 366.

EXAMPLE 39

3-(3,5-Difluoropyridin-2-yl)-5-[3-(3,5-difluoropyridin-2-yl)-4-fluorophenyl]-[1,2,4]triazine A solution of 5-(3-bromo-4-fluorophenyl)-3-methylsulfanyl-[1,2,4]triazine and 3,5-difluoro-2-tributylstannylpyridine were coupled together by the method of Example 36 to give 3-(3,5-difluoropyridin-2-yl)-5-[3-(3,5-difluoropyridin-2-yl)-4-fluorophenyl]-[1,2,4]triazine: $\delta_H$ (500 MHz, CDCl$_3$) 7.38–7.46 (3H, m), 8.44–8.48 (1H, m), 8.50 (1H, dd, J 2.3, 6.7 Hz), 8.52 (1H, d, J 2.3 Hz), 8.63 (1H, s), 9.77 (1H, s); m/z (ES$^+$) 402.

EXAMPLE 40

3-(4-Chloro-2-fluorophenyl)-5-[4-fluoro-3-(3-fluoropyridin-2-yl)phenyl]-[1,2,4]triazine A solution of 5-[4-fluoro-3-(3-fluoropyridin-2-yl)phenyl]-3-methylsulfanyl-[1,2,4]triazine and 2-(4-chloro-2-fluorophenyl)-4,4,5,5-tetramethyl-[1,3,2]dioxaborolane were coupled together by the method of Example 2 to give 3-(4-chloro-2-fluorophenyl)-5-[4-fluoro-3-(3-fluoropyridin-2-yl)phenyl]-[1,2,4]triazine: $\delta_H$ (500 MHz, CDCl$_3$) 7.30–7.35 (2H, m), 7.40–7.46 (2H, m), 7.53–7.61 (1H, m), 8.26 (1H, t, J 8.2 Hz), 8.42–8.45 (1H, m), 8.54 (1H, dd, J 2.4, 6.6 Hz), 8.62 (1H, d, J 4.6 Hz), 9.69 (1H, s); m/z (ES$^+$) 399.

EXAMPLE 41

3-(3,5-Difluoropyridin-2-yl)-5-[4-fluoro-3-(3-fluoropyridin-2-yl)phenyl]-[1,2,4]triazine A solution of 5-[4-fluoro-3-(3-fluoropyridin-2-yl)phenyl]-3-methylsulfanyl-[1,2,4]triazine and 3,5-difluoro-2-tributylstannylpyridine were coupled together by the method of Example 36 to give 3-(3,5-difluoro-pyridin-2-yl)-5-[4-fluoro-3-(3-fluoropyridin-2-yl)phenyl]-[1,2,4]triazine: $\delta_H$ (500 MHz, CDCl$_3$) 7.34 (1H, m), 7.40–7.48 (2H, m), 7.56–7.60 (1H, m), 8.43–8.46 (1H, m), 8.54 (1H, dd, J 2.4, 6.6 Hz), 8.61 (2H, m), 9.78 (1H, s); m/z (ES$^+$) 384.

What is claimed is:

1. A pharmaceutical composition comprising a pharmaceutically acceptable carrier and a compound of formula I, or an N-oxide thereof or a pharmaceutically acceptable salt thereof:

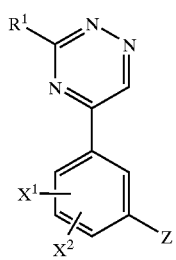

(I)

wherein:
X¹ represents hydrogen, halogen, $C_{1-6}$ alkyl, trifluoromethyl or $C_{1-6}$ alkoxy;
X² represents hydrogen or halogen;
Z represents aryl or heteroaryl, either of which groups may be optionally substituted; and
R¹ represents aryl or heteroaryl, either of which groups may be optionally substituted.

2. The pharmaceutical composition of claim 1 wherein the compound of formula I, X¹ is fluoro.

3. The pharmaceutical composition of claim 1 wherein the compound of formula I, X² is hydrogen.

4. The pharmaceutical composition of claim 1 wherein the compound of formula I, R¹ is an optionally substituted phenyl or pyridyl group.

5. A pharmaceutical composition comprising a pharmaceutically acceptable carrier and a compound which is selected from the group consisting of:

2'-fluoro-5'-(3-phenyl-[1,2,4]triazin-5-yl)biphenyl-2-carbonitrile;
4,2'-difluoro-5'-[3-(4-fluorophenyl)-[1,2,4]triazin-5-yl]biphenyl-2-carbonitrile;
4,2'-difluoro-5'-[3-(2,4-difluorophenyl)-[1,2,4]triazin-5-yl]biphenyl-2-carbonitrile;
4,2'-difluoro-5'-[3-(2-fluorophenyl)-[1,2,4]triazin-5-yl]biphenyl-2-carbonitrile;
4,2'-difluoro-5'-[3-(4-methoxyphenyl)-[1,2,4]triazin-5-yl]biphenyl-2-carbonitrile;
3-(2,4-difluorophenyl)-5-[4-fluoro-3-(3-fluoropyridin-4-yl)phenyl]-[1,2,4]triazine;
5-[4-fluoro-3-(3-fluoropyridin-4-yl)phenyl]-3-(4-methoxyphenyl)-[1,2,4]triazine;
5-[3-(3,5-difluoropyridin-4-yl)-4-fluorophenyl]-3-(2,4-difluorophenyl)-[1,2,4]triazine;
5-[3-(3,5-difluoropyridin-2-yl)-4-fluorophenyl]-3-(4-methoxyphenyl)-[1,2,4]triazine;
6,2'-difluoro-5'-[3-(2,4-difluorophenyl)-[1,2,4]triazin-5-yl]biphenyl-2-carbonitrile;
3-(2,4-difluorophenyl)-5-(2-fluoro-2'-trifluoromethylbiphenyl-5-yl)-[1,2,4]triazine;
5-(2,2'-difluorobiphenyl-5-yl)-3-(2,4-difluorophenyl)-[1,2,4]triazine;
5,2'-difluoro-5'-[3-(2,4-difluorophenyl)-[1,2,4]triazin-5-yl]biphenyl-2-carbonitrile;
3,2'-diffluoro-5'-[3-(2,4-difluorophenyl)-[1,2,4]triazin-5-yl]biphenyl-2-carbonitrile;
3-(2-fluorophenyl)-5-[4-fluoro-3-(pyridin-3-yl)phenyl]-[1,2,4]triazine;
5-[4-fluoro-3-(pyridin-3-yl)phenyl]-3-(4-methoxyphenyl)-[1,2,4]triazine;
3-(2,4-difluorophenyl)-5-[4-fluoro-3-(pyridin-3-yl)phenyl]-[1,2,4]triazine;
5-[4-fluoro-3-(pyridin-2-yl)phenyl]3-(pyridin-2-yl)-[1,2,4]triazine;
5'-[3-(2,4-difluorophenyl)-[1,2,4]triazin-5-yl]-2'-fluorobiphenyl-4-carbonitrile;
3-(2,4-difluorophenyl)-5-[4-fluoro-3-(3-fluoropyridin-2-yl)phenyl]-[1,2,4]triazine;
5-[4-fluoro-3-(3-fluoropyridin-2-yl)phenyl]-3-(4-methoxyphenyl)-[1,2,4]triazine;
5-[4-fluoro-3-(3-fluoropyridin-2-yl)phenyl]-3-(3-fluoropyridin-4-yl)-[1,2,4]triazine;
5-[4-fluoro-3-(3-fluoropyridin-2-yl)phenyl]-3-(3-fluoropyridin-2-yl)-[1,2,4]triazine;
3-(3,5-difluoropyridin-2-yl)-5-[3-(3,5-difluoropyridin-2-yl)-4-fluorophenyl]-[1,2,4]triazine;
3-(4-chloro-2-fluorophenyl)-5-[4-fluoro-3-(3-fluoropyridin-2-yl)phenyl]-[1,2,4]triazine; or
3-(3,5-difluoropyridin-2-yl)-5-[4-fluoro-3-(3-fluoropyridin-2-yl)phenyl]-[1,2,4]triazine;
or a pharmaceutically acceptable salt thereof.

6. A method for the treatment of anxiety in a patient in need thereof which comprises administering to such patient a therapeutically effective amount of a compound of formula I, or an N-oxide thereof or a pharmaceutically acceptable salt thereof:

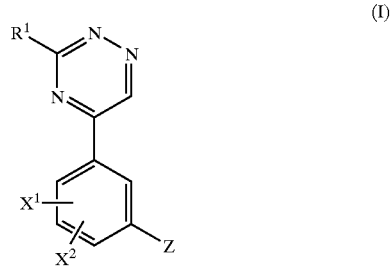

(I)

wherein:
X¹ represents hydrogen, halogen, $C_{1-6}$ alkyl, trifluoromethyl or $C_{1-6}$ alkoxy;
X² represents hydrogen or halogen;
Z represents aryl or heteroaryl, either of which groups may be optionally substituted; and
R¹ represents aryl or heteroaryl, either of which groups may be optionally substituted.

7. The method of claim 6 wherein the compound of formula I, X¹ is fluoro.

8. The method of claim 6 wherein the compound of formula I, X² is hydrogen.

9. The method of claim 6 wherein the compound of formula I, R¹ is an optionally substituted phenyl or pyridyl group.

10. The method of claim 6 wherein the compound is selected from the group consisting of:

2'-fluoro-5'-(3-phenyl-[1,2,4]triazin-5-yl)biphenyl-2-carbonitrile;
4,2'-difluoro-5'-[3-(4-fluorophenyl)-[1,2,4]triazin-5-yl]biphenyl-2-carbonitrile;
4,2'-difluoro-5'-[3-(2,4-difluorophenyl)-[1,2,4]triazin-5-yl]biphenyl-2-carbonitrile;
4,2'-difluoro-5'-[3-(2-fluorophenyl)-[1,2,4]triazin-5-yl]biphenyl-2-carbonitrile;
4,2'-difluoro-5'-[3-(4methoxyphenyl)-[1,2,4]triazin-5-yl]biphenyl-2-carbonitrile;

3-(2,4-difluorophenyl)-5-[4-fluoro-3-(3-fluoropyridin)-4-yl)phenyl]-[1,2,4]triazine;

5-[4-fluoro-3-(3-fluoropyridin-4-yl)phenyl]-3-(4-methoxyphenyl)-[1,2,4]triazine;

5-[3-(3,5-difluoropyridin-4-yl)-4-fluorophenyl]-3-(2,4-difluorophenyl)-[1,2,4]triazine;

5-[3-(3,5-difluoropyridin-2-yl)-4-fluorophenyl]-3-(4-methoxyphenyl)-[1,2,4]triazine;

6,2'-difluoro-5'-[3-(2,4-difluorophenyl)-[1,2,4]triazin-5-yl]biphenyl-2-carbonitrile;

3-(2,4-difluorophenyl)-5-(2-fluoro-2'-trifluoromethylbiphenyl-5-yl)-[1,2,4]triazine;

5-(2,2'-difluorobiphenyl-5-yl)-3-(2,4-difluorophenyl)-[1,2,4]triazine;

5,2'-difluoro-5'-[3-(2,4-difluorophenyl)-[1,2,4]triazin-5-yl]biphenyl-2-carbonitrile;

3,2'-diffluoro-5'-[3-(2,4-difluorophenyl)-[1,2,4]triazin-5-yl]biphenyl-2-carbonitrile;

3-(2-fluorophenyl)-5-[4-fluoro-3-(pyridin-3-yl)phenyl]-[1,2,4]triazine;

5-[4-fluoro-3-(pyridin-3-yl)phenyl]-3-(4-methoxyphenyl)-[1,2,4]triazine;

3-(2,4-difluorophenyl)-5-[4-fluoro-3-(pyridin-3-yl)phenyl]-[1,2,4]triazine;

5-[4-fluoro-3-(pyridin-2-yl)phenyl]-3-(pyridin-2-yl)-[1,2,4]triazine;

5'-[3-(2,4-difluorophenyl)-[1,2,4]triazin-5-yl]-2'-fluorobiphenyl-4-carbonitrile;

3-(2,4-difluorophenyl)-5-[4-fluoro-3-(3-fluoropyridin-2-yl)phenyl]-[1,2,4]triazine;

5-[4-fluoro-3-(3-fluoropyridin-2-yl)phenyl]-3-(4-methoxyphenyl)-[1,2,4]triazine;

5-[4-fluoro-3-(3-fluoropyridin-2-yl)phenyl]-3-(3-fluoropyridin-4-yl)-[1,2,4]triazine;

5-[4-fluoro-3-(3-fluoropyridin-2-yl)phenyl]-3-(3-fluoropyridin-2-yl)-[1,2,4]triazine;

3-(3,5-difluoropyridin-2-yl)-5-[3-(3,5-difluoropyridin-2-yl)-4-fluorophenyl]-[1,2,4]triazine;

3-(4-chloro-2-fluorophenyl)-5-[4-fluoro-3-(3-fluoropyridin-2-yl)phenyl]-[1,2,4]triazine; or 3-(3,5-difluoropyridin-2-yl)-5-[4-fluoro-3-(3-fluoropyridin-2-yl)phenyl]-[1,2,4]triazine;

or a pharmaceutically acceptable salt thereof.

\* \* \* \* \*